United States Patent [19]
Ullrich et al.

[11] Patent Number: 5,895,813
[45] Date of Patent: Apr. 20, 1999

[54] DIAGNOSIS AND TREATMENT OF TKA-1 RELATED DISORDERS

[75] Inventors: Axel Ullrich, Martinsreid, Germany; Klaus Seedorf, Vedbaek, Denmark

[73] Assignee: Max-Planck-Gesellschaft Zur Forderung Der Wissenschaften E.V., Munich, Germany

[21] Appl. No.: 08/665,037

[22] Filed: Jun. 13, 1996

Related U.S. Application Data

[60] Provisional application No. 60/005,167, Oct. 13, 1995.

[51] Int. Cl.$^6$ .............. C12N 1/13; C12N 5/10; C12N 15/63; C12N 15/11
[52] U.S. Cl. .............. 536/23.5; 536/24.1; 536/24.3; 435/320.1; 435/252.3; 435/254.11; 435/325
[58] Field of Search .............. 536/23.5, 24.1, 536/24.3; 435/320.1, 252.3, 254.11, 325

[56] References Cited

U.S. PATENT DOCUMENTS 4,945,050  7/1990  Sanford et al. .............. 435/172.1

FOREIGN PATENT DOCUMENTS 9213001  8/1992  WIPO.
9519169  7/1995  WIPO.

OTHER PUBLICATIONS

George et al. Current methods in sequence comparison and analysis. In Macromolecular Sequencing and Synthesis, D Schlessinger, ed. Alan R Liss, Inc., NY. pp. 127–149, 1988.
Sambrook et al. Molecular Cloning: A Laboratory Manual, 2d ed. CSHL Press, Cold Spring Harbor, NY. pp. 9.50–9.51; 11.3–11.15, 1989.
Hillier et al. y162a05.r1 Homo sapiens cDNA clone 162800 5'. EST–STS Accession No. H27808, Jul. 13, 1995.
Hillier et al. yp07h01.r1 Homo sapiens cDNA clone 186769 5' similiar to contains TAR1 repetitive element. EST–STS Accession No. H51921, Sep. 18, 1995.
Aaronson, "Growth Factors and Cancer," *Science* 254:1146–1153 (1991).
Abe et al., "Molecular Characterization of a Novel Metabotropic Glutamate Receptor mGluR5 Coupled to Inositol Pohosphate/$Ca^{2+}$ Signal," *J. Biol. Chem.* 19:13361–13368 (1992).
Benoist and Chambon, "In vivo sequence requirements of the SV40 early promoter region," *Nature* 290:304–310 (1981).
Blaike et al., "A Region in the Shc Distinct from the SH2 Domain Can bind Tyroxine–phosphorylated Growth Factor Receptors," *J. Biol. Chem.* 269:32031–32034 (1994).
Bosenberg et al., "The Cytoplasmic Carboxy–Terminal Amino Acid Specifies Cleavage of Membrane TGFα into Soluble Growth Factor," *Cell* 71:1157–1165 (1992).
Brinster et al., "Factors Affecting the Efficiency of Introducing Foreign DNA into Mice by Microinjecting Eggs," *Proc. Natl. Acad. Sci. USA* 82:4438–4442 (1985).
Bühring et al., "The Product of the Proto–oncogene c–kit ($P145_{c-kit}$) is a Human Bone Marrow Surface Antigen of Hemopoietic Precursor Cells which is Expressed on a Subset of Acute Non–lymphoblastic Leukemic Cells," *Leukemia* 5(10):854–860 (1991).
Capecchi, "Altering the Genome by Homologous Recombination," *Science* 244:1288–1292 (1989).
Chen and Okayama, "High–Efficiency Transformation of Mammalian Cells by Plasmid DNA," *Mol. and Cell. Biol.* 7(8):2745–2752 (1987).
Curiel et al., "Gene Transfer to Respiratory Epithelial Cells via the Receptor–mediated Endocytosis Pathway," *Am. J. Respir. Cell. Mol. Biol.* 6:247–252 (1992).
Felgner et al., "Lipofection: A Highly Efficient, Lipid–mediated DNA–transfection Procedure," *Proc. Natl. Acad. Sci. USA* 84:7413–7417 (1987).
Felgner and Ringold, "Cationic liposome–mediated transfection," *Nature* 337:387–388 (1989).
Fendly et al., "Characterization of Murine Monoclonal Antibodies Reactive to Either the Human or Epidermal Growth Factor Receptor or HER2/neu Gene Product" *Cancer Research* 50:1550–1558 (1990).
Gorman et al., "The Human Cytomegalovirus Major Immediate Early Promoter Can Be trans–Activated by Adenovirus Early Proteins," *Virology* 171:377–385 (1989).
Gottesman, "Bacterial Regulation: Global Regulatory Networks," *Ann. Rev. Genet.* 18:415–441 (1984).
Hamer and Walling, "Regulation In Vivo of a Cloned Mammalian Gene: Cadmium Induces the Transcription of a Mouse Metallothionein Gene in SV40 Vectors," *J. of Molecular and Applied Genetics* 1:273–288 (1982).
Hammer et al., "Spontaneous Inflammatory Disease in Transgenic Rats Expressing HLA–B27 and Human $\beta_2$m: An Animal Model of HLA–B27–Associated Human Disorders," *Cell* 63:1099–1112 (1990).
Hardie, "Roles of Protein Kinases and Phosphatases in Signal Transduction," *Symp. Soc. Exp. Bio.* 44:241–255 (1990).
Heinemann and Hahn, Circular permutations of protein sequence: not so rare? *TIBS* 20:349–350 (1995).
Herbst et al., "Substrate Phosphorylation Specificity of the Human c–kit Receptor Tyrosine Kinase," *J. of Biol. Chem.* 266(30):19908–19916 (1991).

(List continued on next page.)

*Primary Examiner*—Elizabeth C. Kemmerer
*Attorney, Agent, or Firm*—Lyon & Lyon LLP

[57] ABSTRACT

The present invention relates to TKA-1 polypeptides, nucleic acids encoding such polypeptides, cells, tissues and animals containing such nucleic acids, antibodies to such polypeptides, assays utilizing such polypeptides, and methods relating to all of the foregoing. Methods for treatment diagnosis, and screening are provided for TKA-1 related diseases or conditions characterized by an abnormal interaction between a TKA-1 polypeptide and a TKA-1 binding partner.

16 Claims, 6 Drawing Sheets

OTHER PUBLICATIONS

Honegger et al., "Evidence that autophosphorylation of solubilized receptors for epidermal growth factor is mediated by intermolecular cross–phosphorylation." *Proc. Natl. Acad. Sci. USA* 86:925–929 (1989).

Houdebine and Chourrout, "Transgenesis in Fish." *Experientia* 47:891–897 (1991).

Huang et al., "Hypertension in mice lacking the gene for endothelial nitric oxide synthase." *Nature* 377:239–242 (1995).

Johnston and Hopper, "Isolation of the yeast regulatory gene GAL4 and analysis of its dosage effects on the galactose/melibiose regulon." *Proc. Natl. Acad. Sci. USA* 79:6971–6975 (1982).

Joyner et al., "Production of a mutation in mouse En–2 gene by homologous recombination in embryonic stem cells." *Nature* 338:153–156 (1989).

Kim et al., "PDGF Stimulation of Inositol Phospholipid Hydrolysis Requires PLC–Vγ1 Phosphorylation on Tyrosine Residues 783 and 1254." *Cell* 65:435–441 (1991).

Klingensmith et al., "The Drosophila segment polarity gene dishevelled encodes a novel protein required for response to the wingless signal." *Genes & Development* 8:118–130 (1994).

Koch et al., "SH2 and SH3 Domains: Elements That Control Interactions of Cytoplasmic Signaling Proteins." *Science* 252:668–674 (1991).

Koonin et al., "dlg–R proteins: modified guanylate kinases." *Nature Genetics* 2:256–257 (1992).

Kornau et al., "Domain Interactions Between NMDA Receptor Subunits and the Postsynaptic Density Protein PSD–95." *Science* 269:1737–1740 (1995).

Kris et al., "Antibodies against a Synthetic Peptide as a Probe for the Kinase Activity of the Avian EGF Receptor and v–erbB Protein." *Cell* 40:619–625 (1985).

Lee et al., "HER2 cytoplasmic domain generates normal mitogenic and transforming signals in a chimeric receptor." *EMBO J.* 8:167–173 (1989).

Macgregor et al., "Direct cloning of leucine zipper proteins: Jun binds cooperatively to the CRE with CRE–BP1." *Oncogene* 5:451–458 (1990).

Maekawa, Kazuhiko et al., "Molecular cloning of a novel protein–tyrosine phosphatase containing a membrane–binding domain and GLGF repeats." *FEBS* 337:200–206 (1994).

Margolis et al., "Effect of Phospholipase C–65 Overexpression on PDGF–Induced Second Messengers and Mitogenesis." *Science* 248:607–610 (1990).

Margolis et al., "EGF Induces Tyrosine Phosphorylation of Phospholipase C–II: A Potential Mechanism for EGF Receptor Signaling." *Cell* 57:1101–1107 (1989).

Mayer et al., "A novel viral oncogene with structural similarity to phospholipase C." *Nature* 332:272–275 (Mar. 1988).

McKnight, "Functional Relationships between Transcriptional Control Signals of the Thymidine Kinase Gene of Herpes Simplex Virus." *Cell* 31:355–365 (1982).

Miller, "Human gene therapy comes of age." *Nature* 357:455–460 (1992).

Miller et al., "Generation of Helper–Free Amphotropic Retroviruses That Transduce a Dominant–Acting, Metotrexate–Resistant Dihydrofolate Reductase Gene." *Molecular Cell Biology* 5:431–437 (1985).

Mulligan, "The Basic Science of Gene Therapy." *Science* 260:926–932 (1993).

Nelson et al., "Detection of Acridinium Esters by Chemiluminescence." *Nonisotopic DNA Probe Techniques* ed. L.J. Kricka (San Diego: Academic Press, Inc. pp. 275–310 (1992).

Nishibe et al., "Increase of the Catalytic Activity of Phospholipase C–γ1 by Tyrosine Phosphorylation." *Science* 250:1253–1256 (1990).

Pawson and Schlessinger, "SH2 and SH3 domains." *Current Biology* 3(7):434–441 (1993).

Pawson and Gish, "SH2 and SH3 Domains: From Structure to Function." *Cell* 71:359–362 (1992).

Ponting and Phillips, "DHR domains in syntrophins, neuronal NO synthases and other intracellular proteins." *TIBS* 20:102–103 (1995).

Posada and Cooper, "Molecular Signal Integration. Interplay Between Serine, threonine and Tyrosine Phosphorylation." *Mol. Biol. of the Cell* 3:583–592 (1992).

Pursel et al., "Genetic Engineering of Livestock." *Science* 244:1281–1288 (1989).

Ridley and Hall, "The Small GTP–Binding Protein rho Regulates the Assembly of Focal Adhesions and Actin Stress Fibers in Response to Growth Factors," *Cell* 70:389–399 (1992).

Ridley et al., "The Small GTP–Binding Protein rac Regulates Growth Factor–Induced Membrane Ruffling." *Cell* 70:401–410 (1992).

Ronnstrand et al., "Characterization of Two Monoclonal Antibodies Reactive with the External Domain on the Platelet–derived Growth Factor Receptor." *J. Biol. Chem.* 263(21):10429–10425 (1989).

Sadowski et al., A Noncatalytic Domain Conserved among Cytoplasmic Protein–Tyrosine Kinases Modifies the Kinase Function and Transforming Activity of Fujinami Sarcoma Virus P130$^{gag-fps}$. *Mol. and Cell. Biol.* 6(12):4396–4408 (1986).

Schlessinger and Ullrich, "Growth Factor Signalling by Receptor Tyrosine Kinases." *Neuron* 9:383–391 (1992).

Schlessinger, "Signal transduction by allosteric receptor oligomerization." *Trends Biochem. Sci.* 13:443–447 (1988).

Seedorf et al., "Analysis of Platelet–derived Growth Factor Receptor Domain Function Using a Novel Chimeric Receptor Approach." *J. Biol. Chem.* 266:12424–12431 (1991).

Seedorf et al., "Differential Effects of Carboxy–Terminal Sequence Deletions on Platelet–Derived Growth Factor Receptor Signaling Activities and Interactions with Cellular Substrates." *Molecular Cell Biology* 12:4347–4356 (1992).

Silver et al., "Amino terminus of the yeast GAL4 gene product is sufficient for nuclear localization." *Proc. Natl. Acad. Sci. USA* 81:5951–5955 (1984).

Snyder, "No endothelial NO." *Nature* 377:196–197 (1995).

Ullrich and Schlessinger, "Signal Transduction by Receptors with Tyrosine Kinase Activity." *Cell* 61:203–212 (1990).

van der Geer and Pawson, "The PTB domain: a new protein module implicated in signal transduction." *TIBS* 20:277–280 (1995).

Weinman et al., "CAMP–mediated Inhibition of the Renal Brush Border membrane Na$^+$–H$^+$ Exchanger Requires a Dissociable Phosphoprotein Cofactor." *Jrnl Clinical Investigation* 92:1781–1786 (1993).

Weinman et al., "Characterization of a Protein Cofactor That Mediates Protein Kinase A Regulation of the Renal Brush Border Membrane Na$^+$–H$^+$ Exchange." *Jrnl Clinical Investigation* 95:2143–2149 (1995).

Yang et al., "In Vivo and In Vitro Gene Transfer to Mammalian Somatic Cells by Particle Bombardment." *Proc. Natl. Acad. Sci. USA* 87:9568–9572 (1990).

Yarden and Ullrich, "Growth factor receptor tyrosine kinase." *Ann. Rev. Biochem.* 57:443–478 (1988).

```
                              GCC GCC GCT GAA GCC ACC GCC GGG TGC CCA GCG CCG CCG CCC CCG AGC
                                  9              18              27              36              45

Met Ala Ala Pro
                              TCC CCC GCG CCC CTG CCC GCG GGC CGG TGG GCA GCG GGC GCC ATG GCC GCG CCG
                                      60              69              78              87              96             105

Glu Pro Leu Arg Pro Arg Leu Cys Arg Leu Val Arg Gly Glu Gln Gly Tyr Gly Phe
                              GAG CCG CTG CGG CCG CGC CTG TGC CGC TTG GTG CGC GGA GAG CAG GGC TAC GGC TTC
                                     117             126             135             144             153             162

His Leu His Gly Glu Lys Gly Arg Arg Gly Gln Phe Ile Arg Arg Val Glu Pro Gly
                              CAC CTG CAC GGC GAG AAG GGC CGC CGC GGC CAG TTC ATC CGG CGC GTG GAA CCC GGT
                                     174             183             192             201             210             219

Ser Pro Ala Glu Ala Leu Ala Ala Gly Asp Arg Leu Val Glu Val Asn Gly Val
                              TCC CCC GCC GAG GCC CTG GCT GGG GAC CGC CTG GTC GAG GTC AAC GGC GTC
                                     231             240             249             258             267             276

Asn Val Glu Gly Glu Thr His His Gln Val Val Gln Arg Ile Lys Ala Val Glu Gly
                              AAC GTG GAG GGC GAG ACG CAC CAC CAG GTG GTG CAA AGG ATC AAC GCT GTG GAG GGG
                                     288             297             306             315             324             333
```

FIG. 1A

| | | | | | | | | | | | | | | |
|---|---|---|---|---|---|---|---|---|---|---|---|---|---|---|
| Gln | Thr | Arg | Leu | Val | Val | Asp | Gln | Glu | Thr | Asp | Glu | Glu | Leu | Arg | Arg | Arg | Gln |
| CAG | ACT | CGG | CTG | GTG | GTG | GAC | CAG | GAG | ACA | GAT | GAG | GAG | CTC | CGC | CGG | CAG |
| | 345 | | | 354 | | | 363 | | | 372 | | | 381 | | | 390 |

| Leu | Thr | Cys | Thr | Glu | Glu | Met | Ala | Gln | Arg | Gly | Leu | Pro | Pro | Ala | His | Asp | Pro | Trp |
|---|---|---|---|---|---|---|---|---|---|---|---|---|---|---|---|---|---|---|
| CTG | ACC | TGT | ACC | GAG | GAG | ATG | GCC | CAG | CGA | GGG | CTC | CCA | CCC | GCC | CAC | GAC | CCC | TGG |
| | 402 | | | 411 | | | 420 | | | 429 | | | 438 | | | 447 |

| Glu | Pro | Lys | Pro | Asp | Trp | Ala | His | Thr | Gly | Ser | His | Ser | Ser | Glu | Ala | Gly | Lys | Lys |
|---|---|---|---|---|---|---|---|---|---|---|---|---|---|---|---|---|---|---|
| GAG | CCG | AAG | CCA | GAC | TGG | GCA | CAC | ACC | GGC | AGC | CAC | AGC | TCC | GAA | GCT | GGC | AAG | AAG |
| | 459 | | | 468 | | | 477 | | | 486 | | | 495 | | | 504 |

| Asp | Val | Ser | Gly | Pro | Leu | Arg | Glu | Leu | Arg | Pro | Arg | Leu | Cys | His | Leu | Arg | Lys | Gly |
|---|---|---|---|---|---|---|---|---|---|---|---|---|---|---|---|---|---|---|
| GAT | GTC | AGT | GGG | CCC | CTG | AGG | GAG | CTG | CGC | CCT | CGG | CTC | TGC | CAC | CTG | CGA | AAG | GGA |
| | 516 | | | 525 | | | 534 | | | 543 | | | 552 | | | 561 |

| Pro | Gln | Gly | Tyr | Gly | Phe | Asn | Leu | His | Ser | Asp | Lys | Ser | Arg | Pro | Gly | Gln | Tyr | Ile |
|---|---|---|---|---|---|---|---|---|---|---|---|---|---|---|---|---|---|---|
| CCT | CAG | GGC | TAT | GGG | TTC | AAC | CTG | CAT | AGT | GAC | AAG | TCC | CGG | CCC | GGC | CAG | TAC | ATC |
| | 573 | | | 582 | | | 591 | | | 600 | | | 609 | | | 618 |

| Arg | Ser | Val | Asp | Pro | Gly | Ser | Pro | Ala | Ala | Arg | Ser | Gly | Leu | Arg | Ala | Gln | Asp | Arg |
|---|---|---|---|---|---|---|---|---|---|---|---|---|---|---|---|---|---|---|
| CGC | TCT | GTG | GAC | CCG | GGC | TCA | CCT | GCC | GCC | CGC | TCT | GGC | CTC | CGC | GCC | CAG | GAC | CGG |
| | 630 | | | 639 | | | 648 | | | 657 | | | 666 | | | 675 |

FIG. 1B

```
Leu Ile Glu Val Asn Gly Gln Asn Val Glu Gly Leu Arg His Ala Glu Val Val Ala
CTC ATT GAG GTG AAC GGG CAG AAT GTG GAG GGA CTG CGC CAT GCT GAG GTG GTG GCC
            687                 696                 705                 714                 723                 732

Ser Ile Lys Ala Arg Glu Asp Glu Ala Arg Leu Val Val Asp Pro Glu Thr Asp
AGC ATC AAG GCA CGG GAG GAC GAG GCC CGG CTG GTC GTG GAC CCC GAG ACA GAT
            744                 753                 762                 771                 780                 789

Glu His Phe Lys Arg Leu Arg Val Thr Pro Thr Glu His Val Glu Gly Pro Leu
GAA CAC TTC AAG CGG CTT CGG GTC ACA CCC ACC GAG CAC GTG GAA GGT CCT CTG
            801                 810                 819                 828                 837                 846

Pro Ser Pro Val Thr Asn Gly Thr Ser Pro Ala Gln Leu Asn Gly Gly Ser Ala Cys
CCG TCA CCC GTC ACC AAT GGA ACC AGC CCT GCC CAG CTC AAT GGT GGC TCT GCG TGC
            858                 867                 876                 885                 894                 903

Ser Ser Arg Ser Asp Leu Pro Gly Ser Asp Lys Asp Thr Glu Asp Gly Ser Ala Trp
TCA TCC CGA AGT GAC CTG CCT GGT TCC GAC AAG GAC ACT GAG GAT GGC AGT GCC TGG
            915                 924                 933                 942                 951                 960

Lys Gln Asp Pro Phe Gln Glu Ser Gly Leu His Ser Pro Thr Ala Ala Glu Ala
AAG CAA GAT CCC TTC CAG GAG AGC GGC CTC CAC AGC CCC ACG GCG GCC GAG GCA
            972                 981                 990                 999                 1008                1017

Arg Arg Leu Glu Pro Cys Glu Ser Thr Ser Ala Arg His Arg Trp Thr Gly Thr
AGG AGA CTC GAG CCA TGC GAG TCA ACA AGC GCG CGC CAC AGA TGG ACT GGA ACA
            1029                1038                1047                1056                1065                1074
```

FIG. 1C

```
Gly Ser Val Lys Ser Ser Ala Thr Ser Glu Pro Leu Pro Ala Cys Leu Gly Thr Leu
GGA AGC GTG AAA TCT TCA GCA ACT TCT GAG CCT CTT GCC TGT CTC GGG ACC CTG
        1086                1095               1104              1113              1122              1131

Gly Pro Leu Pro His Gly Pro Trp Ala Ser Ala Cys Pro Glu Leu Pro Gln Pro Gln
GGA CCC CTC CCG CAC GGA CCT TGG GCC TCA GCC TGC CCC GAG CTC CCC CAG CCT CAG
        1143              1152              1161              1170              1179              1188

Trp Thr Gly Gly Trp Ser Cys His Cys Pro Glu Ile Ser Pro Gly Glu Pro
TGG ACT GGA GGG TGG TCC TGC CAT TGC CCA GAA ATC AGC CCC GGT GAG CCC
        1200              1209              1218              1227              1236              1245

Pro Ser Cys Pro Cys Pro Pro Gly Thr Gly Gly Leu Trp Gln Gln Asp Arg Gly Arg
CCA TCC TGC CCC TGC CCA CCA GGT ACT GGG GGC CTG TGG CAG CAA GAT AGG GGG AGA
        1257              1266              1275              1284              1293              1302

Glu Thr Gln Arg Cys Glu Arg Glu Arg Ser Glu Thr Glu Thr Glu Arg Glu Arg Arg
GAG ACC CAG AGA TGT GAG AGA GAG AGA TCA GAG GAG ACA GAG GAG AGA GAG AGA AGA
        1314              1323              1332              1341              1350              1359

His Arg Glu Arg Gln Arg Glu Arg Glu Ser Glu Arg Arg Ala Arg Gly Ser Arg Ala
CAC AGA GAG AGA CAG AGA GAG AGA GAG AGC GAG CGA CGG GCG CGC AGC CGC AGG GCC
        1371              1380              1389              1398              1407              1416
```

FIG. 1D

```
Phe Ala Ala Leu Pro Gly Pro Ala Asp TER
TTT GCT GCT CTG CCG GGG CCT GCT GAC TGA AAG GAA TTT GTG TTT TTG CTT TTT TTC
        1428            1437            1446            1455            1464            1473

CAA AAA GAT CTC CAG CTC CAC ACA TGT TTC CAC TTA ATA CCA GAG ACC CCC CCC TTC
        1485            1494            1503            1512            1521            1530

CCC TCC CCC TTC CCC TCC CCC TTG GGA CGC GCT CTA AAT AAT AAT TGC AAT AAA ACA AAC
        1542            1551            1560            1569            1578            1587

CTT TCT CTG CAA AAA AAA AAA AAA AAA AAA AAA AAA AAA AAA AAA AAA AAA AAA AAA A
        1599            1608            1617            1626            1635
```

DIAGNOSIS AND TREATMENT OF TKA-1 RELATED DISORDERS

CROSS-REFERENCE TO RELATED APPLICATIONS

This application is related to provisional application Serial No. 60/005,167, filed Oct. 13, 1995, which is incorporated herein by reference in its entirety, including any drawings and figures.

FIELD OF THE INVENTION

The present invention relates to the novel protein termed tyrosine kinase associated protein one ("TKA-1"), nucleotide sequences encoding TKA-1, as well as various products and methods useful for the diagnosis and treatment of various TKA-1 related diseases and conditions.

BACKGROUND OF THE INVENTION

The following description of the background of the invention is provided to aid in understanding the invention but is not admitted to be prior art to the invention.

Cellular signal transduction is a fundamental mechanism whereby external stimuli that regulate diverse cellular processes are relayed to the interior of cells. One of the key biochemical mechanisms of signal transduction involves the reversible phosphorylation of tyrosine residues on proteins. The phosphorylation state of a protein is modified through the reciprocal actions of tyrosine kinases (TKs) and tyrosine phosphatases (TPs).

Receptor tyrosine kinases (RTKs) belong to a family of transmembrane proteins and have been implicated in cellular signaling pathways. The predominant biological activity of some RTKs is the stimulation of cell growth and proliferation, while other RTKs are involved in arresting growth and promoting differentiation. In some instances, a single tyrosine kinase can inhibit, or stimulate, cell proliferation depending on the cellular environment in which it is expressed. (Schlessinger and Ullrich, *Neuron*, 9(3):383–391, 1992.) The platelet derived growth factor receptor (PDGF-R) and the role of its ligand (i.e., PDGF) in cancer are described in International Patent Application WO 95/19169, published Jul. 20, 1995, incorporated herein by reference in its entirety including any drawings.

RTKs are composed of at least three domains: an extracellular ligand binding domain, a transmembrane domain and a cytoplasmic catalytic domain that can phosphorylate tyrosine residues. (Yarden and Ullrich, *Ann. Rev. Biochem.* 57:443–478, 1988) Ligand binding to membrane-bound receptors induces the formation of receptor dimmers and allosteric changes that activate the intracellular kinase domains and result in the self-phosphorylation (autophosphorylation and/or transphosphorylation) of the receptor on tyrosine residues. Their intrinsic tyrosine kinase is activated upon ligand binding, thereby initiating a complex signal transduction pathway that begins with receptor autophosphorylation and culminates in the tyrosine phosphorylation of a variety of cellular substrates and ultimately in the initiation of nuclear events necessary for the overall cell response (Schlessinger and Ullrich, *Neuron* 9:383–391, 1992). Individual phosphotyrosine residues of the cytoplasmic domains of receptors may serve as specific binding sites that interact with a host of cytoplasmic signaling molecules, thereby activating various signal transduction pathways (Ullrich and Schlessinger, *Cell* 61:203–212, 1990).

The intracellular, cytoplasmic, non-receptor protein tyrosine kinases do not contain a hydrophobic transmembrane domain or an extracellular domain and share non-catalytic domains in addition to sharing their catalytic kinase domains. Such non-catalytic domains include the SH2 domains (SRC homology domain 2; Sadowski et al., *Mol. Cell. Biol.* 6:4396–4408; Koch et al., *Science* 252:668–674, 1991) SH3 domains (SRC homology domain 3; Mayer et al., *Nature* 332:269–272, 1988) and PI (also called PTB) domains (Blaike, et al., *JBC* 269:32031–32034, 1994; VanderGeer and Pawson *TIBS* 20: 277–280, 1995). The non-catalytic domains are thought to be important in the regulation of protein-protein interactions during signal transduction (Pawson and Gish, *Cell* 71:359–362, 1992).

A central feature of signal transduction (for reviews, see Posada and Cooper, *Mol. Biol. Cell* 3:583–392, 1992; Hardie, *Symp. Soc. Exp. Biol.* 44:241–255, 1990), is the reversible phosphorylation of certain proteins. Receptor phosphorylation stimulates a physical association of the activated receptor with target molecules. Some of the target molecules such as phospholipase Cγ are in turn phosphorylated and activated. Margolis et al., *Cell* 57:1101–1107, 1989; Margolis et al., *Science* 248:607–610, 1990; Nishibe et al., *Science* 250:1253–1255, 1990; and Kim et al., *Cell* 65:435–411, 1991. Such phosphorylation transmits a signal to the cytoplasm. Other target molecules are not phosphorylated, but assist in signal transmission by acting as adapter molecules for secondary signal transducer proteins. For example, receptor phosphorylation and the subsequent allosteric changes in the receptor recruit the Grb-2/SOS complex to the catalytic domain of the receptor where its proximity to the membrane allows it to activate ras. Pawson and Schlessinger, *Current Biol.* 13:434, 1993.

Receptor phosphorylation is essential for binding and phosphorylation of cytoplasmic target proteins that contain src homology region 2 (SH2) domains, such as phospholipase Cγ (PLCγ), p21$^{ras}$ GTPase-activating protein (GAP), phosphatidylinositol (PI) 3'-kinase (PI3K), p60$^{src}$ and related tyrosine kinases, growth factor receptor-bound protein 2 (GRB-2), vav, SHC, CRK, NCK, and PTP1D, (also called SH-PTP2 or syp) and for proteins that contain PI domains, such as SHC. High affinity binding of these signal-transducing factors is strictly dependent on SH2 domains and tyrosine-phosphorylated, short sequence motifs within different domains of the receptor tyrosine kinase (Koch, C. A. et al., (1991), *Science*, 252, 668–674).

The secondary signal transducer molecules generated by activated receptors result in a signal cascade that regulates cell functions such as cell division or differentiation. Reviews describing intracellular signal transduction include Aaronson, *Science*, 254:1146–1153, 1991; Schlessinger, *Trends Biochem. Sci.*, 13:443–447, 1988; and Ullrich and Schlessinger, *Cell*, 61:203–212, 1990. However, the search for receptor-specific signal transducers and regulators which (in addition to generally employed SH2 domain substrate proteins) define ligand- and cell type-characteristic effects has so far had only limited success.

SUMMARY OF THE INVENTION

The present invention relates to TKA-1 polypeptides, nucleic acids encoding such polypeptides, cells containing such nucleic acids, antibodies to such polypeptides, assays utilizing such polypeptides, and methods relating to all of the foregoing. The present invention is based upon the isolation and characterization of a new protein which we have designated TKA-1.

A cDNA clone encoding a novel type of tyrosine kinase-associated protein, designated TKA-1, was isolated from a λgt11 library. The TKA-1 cDNA encodes a protein of 47 kD, which specifically interacts with C-terminal sequences of the PDGF-R in a ligand-independent fashion without becoming tyrosine-phosphorylated itself. In vitro association experiments indicate that TKA-1, which is widely expressed in normal tissues and tumor cells, interacts tightly and specifically with the PDGF-R in spite of the absence of SH2 or PI domains. TKA-1 binding to structural determinants within the receptor's C-terminal tail results in ligand-independent receptor autophosphorylation, substrate phosphorylation, and activation of receptor-associated phosphatidylinositol (PI) 3'-kinase. TKA-1 overexpression enhances DNA synthesis in NIH3T3 fibroblasts and results in disintegration of actin filaments, similar to the transient effect caused by PDGF in nontransfected NIH 3T3 cells. Structural characteristics and functional properties establish TKA-1 as a novel type of intracellular polypeptide involved in receptor-specific regulation of cellular signals.

Thus, in a first aspect the invention features an isolated, enriched, or purified nucleic acid encoding a TKA-1 polypeptide.

By "TKA-1 polypeptide" is meant an amino acid sequence substantially similar to the sequence shown in FIG. 1A–4F (SEQ ID No: 2), or fragments thereof. A sequence that is substantially similar will preferably have at least 90% identity (more preferably at least 95% and most preferably 99–100) to the sequence of FIG. 1A–4F (SEQ ID No: 2).

By "identity" is meant a property of sequences that measures their similarity or relationship. Identity is measured by dividing the number of identical residues by the total number of residues and multiplying the product by 100. Thus, two copies of exactly the same sequence have 100% identity, but sequences that are less highly conserved and have deletions, additions, or replacements may have a lower degree of identity. Those skilled in the art will recognize that several computer programs are available for determining sequence identity.

By "isolated" in reference to nucleic acid is meant a polymer of 6 (preferably 21, more preferably 39, most preferably 75) or more nucleotides conjugated to each other, including DNA or RNA that is isolated from a natural source or that is synthesized. In certain embodiments of the invention longer nucleic acids are preferred, for example those of 300, 600, 900 or more nucleotides and/or those having at least 50%, 60%, 75%, 90%, 95% or 99% identity to the full length sequence shown in FIG. 1A–4F (SEQ ID No: 1). The isolated nucleic acid of the present invention is unique in the sense that it is not found in a pure or separated state in nature. Use of the term "isolated" indicates that a naturally occurring sequence has been removed from its normal cellular (i.e., chromosomal) environment. Thus, the sequence may be in a cell-free solution or placed in a different cellular environment. The term does not imply that the sequence is the only nucleotide chain present, but that it is essentially free (about 90–95% pure at least) of non-nucleotide material naturally associated with it and thus is meant to distinguish from isolated chromosomes.

By the use of the term "enriched" in reference to nucleic acid is meant that the specific DNA or RNA sequence constitutes a significantly higher fraction (2–5 fold) of the total DNA or RNA present in the cells or solution of interest than in normal or diseased cells or in the cells from which the sequence was taken. This could be caused by a person by preferential reduction in the amount of other DNA or RNA present, or by a preferential increase in the amount of the specific DNA or RNA sequence, or by a combination of the two. However, it should be noted that enriched does not imply that there are no other DNA or RNA sequences present, just that the relative amount of the sequence of interest has been significantly increased. The term significant here is used to indicate that the level of increase is useful to the person making such an increase, and generally means an increase relative to other nucleic acids of about at least 2 fold, more preferably at least 5 to 10 fold or even more. The term also does not imply that there is no DNA or RNA from other sources. The other source DNA may, for example, comprise DNA from a yeast or bacterial genome, or a cloning vector such as pUC19. This term distinguishes from naturally occurring events, such as viral infection, or tumor type growths, in which the level of one mRNA may be naturally increased relative to other species of mRNA. That is, the term is meant to cover only those situations in which a person has intervened to elevate the proportion of the desired nucleic acid.

It is also advantageous for some purposes that a nucleotide sequence be in purified form. The term "purified" in reference to nucleic acid does not require absolute purity (such as a homogeneous preparation); instead, it represents an indication that the sequence is relatively purer than in the natural environment (compared to the natural level this level should be at least 2–5 fold greater, e.g., in terms of mg/ml). Individual clones isolated from a cDNA library may be purified to electrophoretic homogeneity. The claimed DNA molecules obtained from these clones could be obtained directly from total DNA or from total RNA. The cDNA clones are not naturally occurring, but rather are preferably obtained via manipulation of a partially purified naturally occurring substance (messenger RNA). The construction of a cDNA library from mRNA involves the creation of a synthetic substance (cDNA) and pure individual cDNA clones can be isolated from the synthetic library by clonal selection of the cells carrying the cDNA library. Thus, the process which includes the construction of a cDNA library from mRNA and isolation of distinct cDNA clones yields an approximately $10^6$-fold purification of the native message. Thus, purification of at least one order of magnitude, preferably two or three orders, and more preferably four or five orders of magnitude is expressly contemplated.

By "a TKA-1 polypeptide" is meant 25 (preferably 30, more preferably 35, most preferably 40) or more contiguous amino acids set forth in the full length amino acid sequence of FIG. 1A–F (SEQ ID NO: 2), or a functional derivative thereof as described herein. In certain aspects, polypeptides of 100, 200, 300 or more amino acids are preferred. The TKA-1 polypeptide can be encoded by a full-length nucleic acid sequence or any portion of the full-length nucleic acid sequence, so long as a functional activity of the polypeptide is retained. Such functional activity can be, for example: (1) stimulation of ligand-independent receptor autophosphorylation, (2) substrate phosphorylation, (3) activation of receptor-associated phosphatidylinositol (PI) 3'-kinase, (4) enhanced DNA synthesis in NIH3T3 fibroblasts and (5) disintegration of actin filaments and (6) receptor dimerization.

In preferred embodiments the isolated nucleic acid comprises, consists essentially of, or consists of a nucleic acid sequence set forth in the full length nucleic acid sequence of FIG. 1A–F (SEQ ID NO: 1), a functional derivative thereof, or encodes at least 25, 30, 35, 40, 50, 100, 200,, or 300 contiguous amino acids thereof; the TKA-1 polypeptide comprises, consists essentially of, or consists of at least 25, 30, 35, or 40 contiguous amino acids of a TKA-1 polypeptide. The nucleic acid may be isolated from a natural source by cDNA cloning or subtractive hybridization; the natural source may be mammalian (human) blood, semen, or tissue and the nucleic acid may be synthesized by the triester method or by using an automated DNA synthesizer. In yet other preferred embodiments the nucleic acid is a conserved or unique region, for example those useful for the design of hybridization probes to facilitate identification and cloning of additional polypeptides, the design of PCR probes to facilitate cloning of additional polypeptides, and obtaining antibodies to polypeptide regions.

By "conserved nucleic acid regions", are meant regions present on two or more nucleic acids encoding a TKA-1 polypeptide, to which a particular nucleic acid sequence can hybridize under lower stringency conditions. Examples of lower stringency conditions suitable for screening for nucleic acid encoding TKA-1 polypeptides are provided in Abe, et al. *J. Biol. Chem.*, 19:13361 (1992) (hereby incorporated by reference herein in its entirety, including any drawings). Preferably, conserved regions differ by no more than 5 out of 20 nucleotides.

By "unique nucleic acid region" is meant a sequence present in a full length nucleic acid coding for a TKA-1 polypeptide that is not present in a sequence coding for any other naturally occurring polypeptide. Such regions preferably comprise 30 or 45 contiguous nucleotides present in the full length nucleic acid encoding a TKA-1 polypeptide. In particular, a unique nucleic acid region is preferably of mammalian origin.

The invention also features a nucleic acid probe for the detection of a TKA-1 polypeptide or nucleic acid encoding a TKA-1 polypeptide in a sample. The nucleic acid probe contains nucleic acid that will hybridize to a sequence set forth in FIG. 1A–F (SEQ ID NO: 1) or a functional derivative thereof.

In preferred embodiments the nucleic acid probe hybridizes to nucleic acid encoding at least 12, 75, 90, 105, 120, 150, 200, 250, 300 or 350 contiguous amino acids of the full-length sequence set forth in FIG. 1A–F (SEQ ID NO: 2) or a functional derivative thereof. Various low or high stringency hybridization conditions may be used depending upon the specificity and selectivity desired. Under stringent hybridization conditions only highly complementary nucleic acid sequences hybridize. Preferably, such conditions prevent hybridization of nucleic acids having 1 or 2 mismatches out of 20 contiguous nucleotides.

Methods for using the probes include detecting the presence or amount TKA-1 RNA in a sample by contacting the sample with a nucleic acid probe under conditions such that hybridization occurs and detecting the presence or amount of the probe bound to TKA-1 RNA. The nucleic acid duplex formed between the probe and a nucleic acid sequence coding for a TKA-1 polypeptide may be used in the identification of the sequence of the nucleic acid detected (for example see, Nelson et al., in *Nonisotopic DNA Probe Techniques*, p. 275 Academic Press, San Diego (Kricka, ed., 1992) hereby incorporated by reference herein in its entirety, including any drawings). Kits for performing such methods may be constructed to include a container means having disposed therein a nucleic acid probe.

The invention also features recombinant nucleic acid, preferably in a cell or an organism. The recombinant nucleic acid may contain a sequence set forth in FIG. 1A–F (SEQ ID NO: 1) or a functional derivative thereof and a vector or a promoter effective to initiate transcription in a host cell. The recombinant nucleic acid can alternatively contain a transcriptional initiation region functional in a cell, a sequence complimentary to an RNA sequence encoding a TKA-1 polypeptide and a transcriptional termination region functional in a cell.

In another aspect the invention features an isolated, enriched, or purified TKA-1 polypeptide.

By "isolated" in reference to a polypeptide is meant a polymer of 2 (preferably 7, more preferably 13, most preferably 25) or more amino acids conjugated to each other, including polypeptides that are isolated from a natural source or that are synthesized. In certain aspects longer polypeptides are preferred, such as those with 402, 407, 413, or 425 contiguous amino acids set forth in FIG. 1A–F. The isolated polypeptides of the present invention are unique in the sense that they are not found in a pure or separated state in nature. Use of the term "isolated" indicates that a naturally occurring sequence has been removed from its normal cellular environment. Thus, the sequence may be in a cell-free solution or placed in a different cellular environment. The term does not imply that the sequence is the only amino acid chain present, but that it is essentially free (about 90–95% pure at least) of non-amino acid material naturally associated with it.

By the use of the term "enriched" in reference to a polypeptide is meant that the specific amino acid sequence constitutes a significantly higher fraction (2 –5 fold) of the total of amino acids present in the cells or solution of interest than in normal or diseased cells or in the cells from which the sequence was taken. This could be caused by a person by preferential reduction in the amount of other amino acids present, or by a preferential increase in the amount of the specific amino acid sequence of interest, or by a combination of the two. However, it should be noted that enriched does not imply that there are no other amino acid sequences present, just that the relative amount of the sequence of interest has been significantly increased. The term significant here is used to indicate that the level of increase is useful to the person making such an increase, and generally means an increase relative to other amino acids of about at least 2 fold, more preferably at least 5 to 10 fold or even more. The term also does not imply that there is no amino acid from other sources. The other source amino acid may, for example, comprise amino acid encoded by a yeast or bacterial genome, or a cloning vector such as pUC19. The term is meant to cover only those situations in which man has intervened to elevate the proportion of the desired nucleic acid.

It is also advantageous for some purposes that an amino acid sequence be in purified form. The term "purified" in reference to a polypeptide does not require absolute purity (such as a homogeneous preparation); instead, it represents an indication that the sequence is relatively purer than in the natural environment (compared to the natural level this level should be at least 2–5 fold greater, e.g., in terms of mg/ml). Purification of at least one order of magnitude, preferably two or three orders, and more preferably four or five orders of magnitude is expressly contemplated. The substance is preferably free of contamination at a functionally significant level, for example 90%, 95%, or 99% pure.

In preferred embodiments the TKA-1 polypeptide contains at least 25, 30, 35, 40, 50, 100, 150, 200, 250, 300, or 350 contiguous amino acids of the full-length sequence set forth in FIG. 1A–4F (SEQ ID NO: 2), or a functional derivative thereof.

In yet another aspect the invention features an antibody (e.g., a monoclonal or polyclonal antibody) having specific binding affinity to a TKA-1 polypeptide. The antibody contains a sequence of amino acids that is able to specifically bind to a TKA-1 polypeptide. By "specific binding affinity" is meant that the antibody binds to TKA-1 polypeptides with greater affinity than it binds to other polypeptides under specified conditions.

Antibodies having specific binding affinity to a TKA-1 polypeptide may be used in methods for detecting the presence and/or amount of a TKA-1 polypeptide in a sample by contacting the sample with the antibody under conditions such that an immunocomplex forms and detecting the presence and/or amount of the antibody conjugated to the TKA-1 polypeptide. Diagnostic kits for performing such methods may be constructed to include a first container means containing the antibody and a second container means having a conjugate of a binding partner of the antibody and a label.

In another aspect the invention features a hybridoma which produces an antibody having specific binding affinity to a TKA-1 polypeptide. By "hybridoma" is meant an immortalized cell line which is capable of secreting an antibody, for example a TKA-1 antibody. In preferred embodiments the TKA-1 antibody comprises a sequence of amino acids that is able to specifically bind a TKA-1 polypeptide.

In another aspect, the invention describes a polypeptide comprising a recombinant TKA-1 polypeptide or a unique fragment thereof. By "unique fragment," is meant an amino acid sequence present in a full-length TKA-1 polypeptide that is not present in any other naturally occurring polypeptide. Preferably, such a sequence comprises 6 contiguous amino acids present in the full sequence. More preferably, such a sequence comprises 12 contiguous amino acids present in the full sequence. Even more preferably, such a sequence comprises 18 contiguous amino acids present in the full sequence By "recombinant TKA-1 polypeptide" is meant to include a polypeptide produced by recombinant DNA techniques such that it is distinct from a naturally occurring polypeptide either in its location (e.g., present in a different cell or tissue than found in nature), purity or structure. Generally, such a recombinant polypeptide will be present in a cell in an amount different from that normally observed in nature.

In another aspect, the invention describes a recombinant cell or tissue containing a purified nucleic acid coding for a TKA-1 polypeptide. In such cells, the nucleic acid may be under the control of its genomic regulatory elements, or may be under the control of exogenous regulatory elements including an exogenous promoter. By "exogenous" it is meant a promoter that is not normally coupled in vivo transcriptionally to the coding sequence for the TKA-1 polypeptide.

In another aspect, the invention features a TKA-1 polypeptide binding agent able to bind to a TKA-1 polypeptide. The binding agent is preferably a purified antibody which recognizes an epitope present on a TKA-1 polypeptide. Other binding agents include molecules which bind to the TKA-1 polypeptide and analogous molecules which bind to a TKA-1 polypeptide. Such binding agents may be identified by using assays that measure TKA-1 binding partner activity, such as those that measure PDGFR activity.

By "purified" in reference to an antibody is meant that the antibody is distinct from naturally occurring antibody, such as in a purified form. Preferably, the antibody is provided as a homogeneous preparation by standard techniques. Uses of antibodies to the cloned polypeptide include those to be used as therapeutics, or as diagnostic tools.

In another aspect, the invention features a method of disrupting or promoting receptor dimerization. The method involves providing a TKA-1 small molecule mimetic (i.e., am organic chemical that mimics the activity of TKA-1 to bind to and activate TKA-1 binding partners) to a TKA-1 binding partner complex. Alternatively, the method may involve providing the full length TKA-1 protein or a large fragment (i.e., at least 80%, or preferably 90% sequence similarity or identity to the full length TKA-1 sequence) thereof to a binding partner. Such a method will preferably aid in tissue regeneration.

In another aspect, the invention features methods of identifying TKA-1 like molecules that have at least one and preferably two or more GLGF or DHR motifs. Such motifs are described in further detailed below and are defined and exemplified in Heinemann and Hahn, *TIBS*, 20:102–104, September 1995, incorporated herein by reference in its entirety including any drawings. Such molecules are believed to be important in receptor dimerization.

Thus, the invention features a method for screening for human cells containing a TKA-1 polypeptide or an equivalent sequence. The method involves identifying the novel polypeptide in human cells using techniques that are routine and standard in the art, such as those described herein for identifying TKA-1 (e.g., cloning, Southern or Northern blot analysis, in situ hybridization, PCR amplification, etc.). Novel methods are also provided which utilize an entire chimera RTK but otherwise are the same as the CORT techniques described in International Patent application WO 92/13001, published Aug. 6, 1992, incorporated herein by reference in its entirety, including any drawings.

The invention also features methods of screening human cells for binding partners of TKA-1 polypeptides and screening other organisms for TKA-1 or the corresponding binding partner. The present invention also features the purified, isolated or enriched versions of the peptides identified by the methods described above.

In another aspect, the invention provides an assay to identify agents capable of interfering with the interaction between TKA-1 and a TKA-1 binding partner or between a TKA-1 like molecule having one or two or more GLGF or DHR domains and a binding partner for such a TKA-1 like molecule. Such assays may be performed in vitro or in vivo and are described in detail in Examples 8–10 herein. Other such assays can be obtained by modifying existing assays. For example the growth assay described in ser. No. 08/487, 088, filed Jun. 7, 1995, now abandoned (incorporated herein by reference including any drawings) may be modified by using the 293 cells described in Example 3 herein.

The summary of the invention described above is non-limiting and other features and advantages of the invention will be apparent from the following description of the preferred embodiments, and from the claims.

BRIEF DESCRIPTION OF THE DRAWINGS

FIG. 1A–F shows the full length nucleic acid sequence (SEQ ID NO:1) and amino acid sequence (SEQ ID NO:2) of TKA -1. The overlined regions of the amino acid sequence (SEQ ID NO:2) represent long and short internal repeats.

DESCRIPTION OF THE PREFERRED EMBODIMENTS

The present invention relates to TKA-1 polypeptides, nucleic acids encoding such polypeptides, cells, tissues and animals containing such nucleic acids, antibodies to such polypeptides, assays utilizing such polypeptides, and methods relating to all of the foregoing.

I. Novel Cloning Methods and Signal Molecules Lacking known Integration Domains We present here the cloning and characterization of cDNA sequences encoding TKA-1, an intracellular factor that selectively binds to PDGFα and β receptors and thereby activates their signaling capacity. Using an activated autophosphorylated receptor chimera consisting of the EGF-R binding and βPDGF-R signaling domains as a probe, one clone was identified in a human placenta λgt11 expression library that encoded a novel binding protein, designated TKA-1, in addition to clones representing mRNA copies for the p85 noncatalytic subunit of PI3K. Because the latter had previously been shown to exhibit very high affinity to the PDGF-R, TKA-1 binding, which occurred under the same experimental conditions during the screening process, appeared to be within a similar range.

Surprisingly, as revealed by cDNA sequencing, the encoded protein did not initially appear to contain an SH2 domain or any other sequence motif known to be involved in protein-protein interactions. Thus, TKA-1 represents a non-SH2 domain-containing factor involved in transmission and regulation of tyrosine kinase signals. Moreover, TKA-1 is not phosphorylated on tyrosines but appears to be constitutively phosphorylated on four Ser/Thr residues resulting in a 53KD form. The existence of two homologous 106 amino acid-long sequences suggests that one TKA-1 molecule may interact simultaneously with two PDGF-R molecules, mediating the generation of a receptor dimer. These homologous sequences have now been identified as GLGF or DHR motifs (see Heinemann and Hahn, *TIBS*, 20:102–104, September 1995, incorporated herein by reference in its entirety including any drawings.

Such motifs are recognized as important binding motifs and are believed to bind to the C terminus of receptors through conserved terminal sequences. PDGF-R conforms to this consensus sequence. References describing these motifs describing their functional importance include Weinman et al., *Jrnl Clinical Investigation* 95:2143–2149, 1995; Weinman et al., *Jrnl Clinical Investigation* 92:1781–1786, 1993; Koonin et al, *Nature Genetics* 2:256–257, 1992; Klingensmith et al., *Genes & Development* 8:118–130, 1994; Kazuhiko et al., *FEBS* 337:200–206, 1994; Kornau et al., *Science* 269:1737–1740, 1995; Snyder, *Nature* 377:196–197, 1995; Huang et al., *Nature* 377:239–242, 1995; Bosenberg et al., *Cell* 71:1157–1165, 1992; and Ponting and Phillips, *TIBS* 20:102–103, 1995 all of which are incorporated herein in their entirety including drawings.

II. PDGF-R Dimerization and Activation

Overexpression of TKA-1 induces biochemical and biological effects normally only induced by ligand-stimulated receptor dimerization and activation. These include receptor autophosphorylation, PI3K binding and activation, the promotion of thymidine incorporation in cellular DNA, and changes in cell morphology normally only observed upon exposure of fibroblasts to PDGF suggesting that TKA-1 may act as an alternative to ligand dependent PDGF-R activation. These effects on the morphology and physiology of cells appear to be caused upon interaction of TKA-1 with C-terminal sequences of the PDGF-R, a region that also contains phosphotyrosine binding sites for SH2 domain signal-transducing proteins such as PLCy and PTP1D (Claesson-Welch, L. (1994), J. Biol. Chem. 269, 32023–32026). Moreover, the 47 kD form of this unusual RTK signal regulator interacts, when associated with cell membranes, with several polypeptides in addition to the receptor.

Overexpression of TKA-1 is accompanied by the constitutive loss of actin filaments, analogous to that induced by exogenous PDGF treatment. Such PDGF-dependent decrease of stress fibers and the appearance of edge ruffles has been reported by several groups. Reports by Ridley, A. J. and Hall A., (1992), *Cell*, 70, 389–399 and Ridley, A. J. et al., (1992), *Cell*, 70, 401–410 showed that actin reorganization to form membrane ruffles is dependent on rac1 and the formation of stress fibers on rho, two small ras-related GTP-binding proteins. This would indicate that in NIH3T3 fibroblasts, both TKA-1 and PDGF activate rac1 and inactivate rho. In TKA-1-expressing cells, inactivation of rho appears to be constitutive, while in normal NIH3T3 fibroblasts the PDGF-induced effect is transient. Although this is a likely explanation, we cannot exclude the possibility that TKA-1 has a direct effect on actin reorganization. While TKA-1 activates the PDGF-R and PDGF-mediated effects to a lesser extent than PDGF, the two factors appear to act additively, suggesting either that TKA-1 and PDGF activate distinct PDGF-R fractions or that simultaneous interaction with extracellular and cytoplasmic receptor sequences results in a hyperactive state.

A potentially more complex role of TKA-1 in signal regulation is suggested by our Northern blot analysis, which revealed the existence of three transcripts of 1.4, 1.6, and 2.2 kb, of which the 1.6 kb form most likely corresponds to our cloned cDNA. The differential expression of these mRNAs in different tissues and even in the same cell type, as shown by the analysis of a panel of mammary carcinoma cell lines, further suggests functional significance for the physiology of the cell and possibly even direct relevance for the pathophysiological state of cancer cells.

In summary, our data show that TKA-1 acts like a PDGF-R-specific intracellular ligand, which upon binding activates tyrosine kinase activity and subsequent effects. Our data suggest the possibility that TKA-1 plays a role in cell survival in the absence of extracellular ligands or in cell locomotion. This is supported by immunofluorescence microscopy on TKA-1 -overexpressing cell lines, which revealed intense localization at cell edges, consistent with signals necessary for cell movement, a process that appears to involve activated PI-3 kinase (Kundra, V. et al., (1994), *Nature*, 367, 474–476). The signal-activating function of TKA-1 suggests novel regulatory mechanisms, which open new possibilities for crosstalk with other receptor and effector systems.

III. Nucleic Acid Encoding A TKA-1 Polypeptide.

Figure 1F:
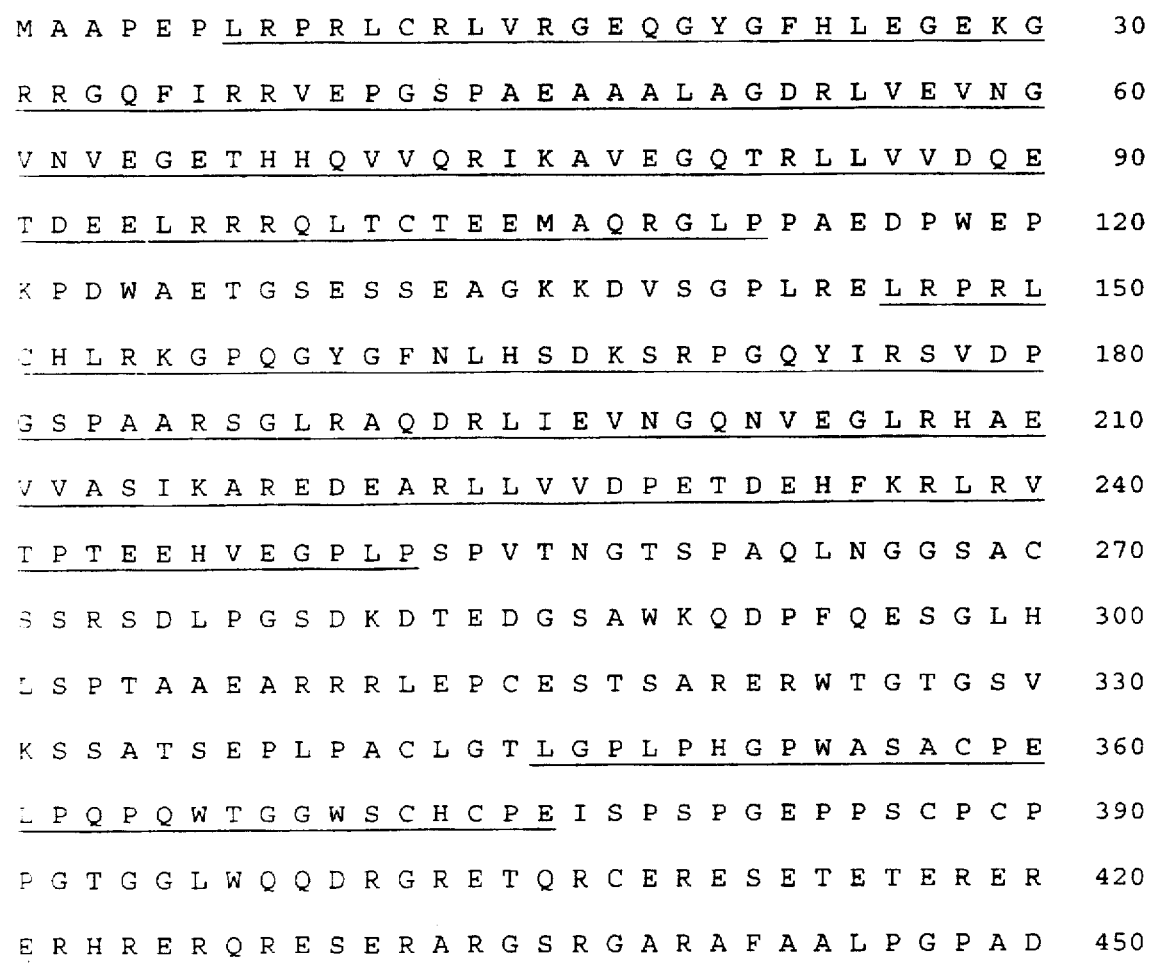

Included within the scope of this invention are the functional equivalents of the herein-described isolated nucleic acid molecules. The degeneracy of the genetic code permits substitution of certain codons by other codons which specify the same amino acid and hence would give rise to the same protein. The nucleic acid sequence can vary substantially since, with the exception of methionine and tryptophan, the known amino acids can be coded for by more than one codon. Thus, portions or all of the TKA-1 gene could be synthesized to give a nucleic acid sequence significantly different from that shown in FIG. 1A–F (SEQ ID NO:1). The encoded amino acid sequence thereof would, however, be preserved.

In addition, the nucleic acid sequence may comprise a nucleotide sequence which results from the addition, deletion or substitution of at least one nucleotide to the 5'-end and/or the 3'-end of the nucleic acid formula shown in FIG. 1A–4F (SEQ ID NO:1) or a derivative thereof. Any nucleotide or polynucleotide may be used in this regard, provided that its addition, deletion or substitution does not alter the amino acid sequence of FIG. 1A–F (SEQ ID NO:2) which is encoded by the nucleotide sequence. For example, the present invention is intended to include any nucleic acid sequence resulting from the addition of ATG as an initiation codon at the 5'-end of the inventive nucleic acid sequence or its derivative, or from the addition of TTA, TAG or TGA as a termination codon at the 3'-end of the inventive nucleotide sequence or its derivative. Moreover, the nucleic acid molecule of the present invention may, as necessary, have restriction endonuclease recognition sites added to its 5'-end and/or 3'-end.

Such functional alterations of a given nucleic acid sequence afford an opportunity to promote secretion and/or processing of heterologous proteins encoded by foreign nucleic acid sequences fused thereto. All variations of the nucleotide sequence of the TKA-1 genes and fragments thereof permitted by the genetic code are, therefore, included in this invention.

Further, it is possible to delete codons or to substitute one or more codons by codons other than degenerate codons to produce a structurally modified polypeptide, but one which has substantially the same utility or activity of the polypeptide produced by the unmodified nucleic acid molecule. As recognized in the art, the two polypeptides are functionally equivalent, as are the two nucleic acid molecules which give rise to their production, even though the differences between the nucleic acid molecules are not related to degeneracy of the genetic code.

IV. A Nucleic Acid Probe for the Detection of TKA-1.

A nucleic acid probe of the present invention may be used to probe an appropriate chromosomal or cDNA library by usual hybridization methods to obtain another nucleic acid molecule of the present invention. A chromosomal DNA or cDNA library may be prepared from appropriate cells according to recognized methods in the art (cf. "Molecular Cloning: A Laboratory Manual", second edition, edited by Sambrook, Fritsch, & Maniatis, Cold Spring Harbor Laboratory, 1989).

In the alternative, chemical synthesis is carried out in order to obtain nucleic acid probes having nucleotide sequences which correspond to N-terminal and C-terminal portions of the amino acid sequence of the polypeptide of interest. Thus, the synthesized nucleic acid probes may be used as primers in a polymerase chain reaction (PCR) carried out in accordance with recognized PCR techniques, essentially according to PCR Protocols, "A Guide to Methods and Applications", edited by Michael et al., Academic Press, 1990, utilizing the appropriate chromosomal or cDNA library to obtain the fragment of the present invention.

One skilled in the art can readily design such probes based on the sequence disclosed herein using methods of computer alignment and sequence analysis known in the art (cf. "Molecular Cloning: A Laboratory Manual", second edition, edited by Sambrook, Fritsch, & Maniatis, Cold Spring Harbor Laboratory, 1989). The hybridization probes of the present invention can be labeled by standard labeling techniques such as with a radiolabel, enzyme label, fluorescent label, biotin avidin label, chemiluminescence, and the like. After hybridization, the probes may be visualized using known methods.

The nucleic acid probes of the present invention include RNA, as well as DNA probes, such probes being generated using techniques known in the art. The nucleic acid probe may be immobilized on a solid support. Examples of such solid supports include, but are not limited to, plastics such as polycarbonate, complex carbohydrates such as agarose and sepharose, and acrylic resins, such as polyacrylamide and latex beads. Techniques for coupling nucleic acid probes to such solid supports are well known in the art.

The test samples suitable for nucleic acid probing methods of the present invention include, for example, cells or nucleic acid extracts of cells, or biological fluids. The sample used in the above-described methods will vary based on the assay format, the detection method and the nature of the tissues, cells or extracts to be assayed. Methods for preparing nucleic acid extracts of cells are well known in the art and can be readily adapted in order to obtain a sample which is compatible with the method utilized.

V. A Probe Based Method And Kit For Detecting TKA-1.

One method of detecting the presence of TKA-1 in a sample comprises a) contacting said sample with the above-described nucleic acid probe, under conditions such that hybridization occurs, and b) detecting the presence of said probe bound to said nucleic acid molecule. One skilled in the art would select the nucleic acid probe according to techniques known in the art as described above. Samples to be tested include but should not be limited to RNA samples of human tissue.

A kit for detecting the presence of TKA-1 in a sample comprises at least one container means having disposed therein the above-described nucleic acid probe. The kit may further comprise other containers comprising one or more of the following: wash reagents and reagents capable of detecting the presence of bound nucleic acid probe. Examples of detection reagents include, but are not limited to radiolabelled probes, enzymatic labeled probes (horse radish peroxidase, alkaline phosphatase), and affinity labeled probes (biotin, avidin, or steptavidin).

In detail, a compartmentalized kit includes any kit in which reagents are contained in separate containers. Such containers include small glass containers, plastic containers or strips of plastic or paper. Such containers allow the efficient transfer of reagents from one compartment to another compartment such that the samples and reagents are not cross-contaminated and the agents or solutions of each container can be added in a quantitative fashion from one compartment to another. Such containers will include a container which will accept the test sample, a container which contains the probe or primers used in the assay, containers which contain wash reagents (such as phosphate buffered saline, Tris-buffers, and the like), and containers which contain the reagents used to detect the hybridized probe, bound antibody, amplified product, or the like. One skilled in the art will readily recognize that the nucleic acid probes described in the present invention can readily be incorporated into one of the established kit formats which are well known in the art.

VI. DNA Constructs Comprising a TKA-1 Nucleic Acid Molecule and Cells Containing These Constructs.

The present invention also relates to a recombinant DNA molecule comprising, 5' to 3', a promoter effective to initiate transcription in a host cell and the above-described nucleic acid molecules. In addition, the present invention relates to a recombinant DNA molecule comprising a vector and an above-described nucleic acid molecules. The present invention also relates to a nucleic acid molecule comprising a transcriptional region functional in a cell, a sequence complimentary to an RNA sequence encoding an amino acid sequence corresponding to the above-described polypeptide, and a transcriptional termination region functional in said cell. The above-described molecules may be isolated and/or purified DNA molecules.

The present invention also relates to a cell or organism that contains an above-described nucleic acid molecule and thereby is capable of expressing a peptide. The polypeptide may be purified from cells which have been altered to express the polypeptide. A cell is said to be "altered to express a desired polypeptide" when the cell, through genetic manipulation, is made to produce a protein which it normally does not produce or which the cell normally produces at lower levels. One skilled in the art can readily adapt procedures for introducing and expressing either genomic, cDNA, or synthetic sequences into either eukaryotic or prokaryotic cells.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene sequence expression. The precise nature of the regulatory regions needed for gene sequence expression may vary from organism to organism, but shall in general include a promoter region which, in prokaryotes, contains both the promoter (which directs the initiation of RNA transcription) as well as the DNA sequences which, when transcribed into RNA, will signal synthesis initiation. Such regions will normally include those 5'-non-coding sequences involved with initiation of transcription and translation, such as the TATA box, capping sequence, CAAT sequence, and the like.

If desired, the non-coding region 3' to the sequence encoding an TKA-1 gene may be obtained by the above-described methods. This region may be retained for its transcriptional termination regulatory sequences, such as termination and polyadenylation. Thus, by retaining the 3'-region naturally contiguous to the DNA sequence encoding an TKA-1 gene, the transcriptional termination signals may be provided. Where the transcriptional termination signals are not satisfactorily functional in the expression host cell, then a 3' region functional in the host cell may be substituted.

Two DNA sequences (such as a promoter region sequence and an TKA-1 sequence) are said to be operably linked if the nature of the linkage between the two DNA sequences does not (1) result in the introduction of a frame-shift mutation, (2) interfere with the ability of the promoter region sequence to direct the transcription of an TKA-1 gene sequence, or (3) interfere with the ability of the an TKA-1 gene sequence to be transcribed by the promoter region sequence. Thus, a promoter region would be operably linked to a DNA sequence if the promoter were capable of effecting transcription of that DNA sequence. Thus, to express an TKA-1 gene, transcriptional and translational signals recognized by an appropriate host are necessary.

The present invention encompasses the expression of the TKA-1 gene (or a functional derivative thereof) in either prokaryotic or eukaryotic cells. Prokaryotic hosts are, generally, very efficient and convenient for the production of recombinant proteins and are, therefore, one type of preferred expression system for the TKA-1 gene. Prokaryotes most frequently are represented by various strains of *E. coli*. However, other microbial strains may also be used, including other bacterial strains.

In prokaryotic systems, plasmid vectors that contain replication sites and control sequences derived from a species compatible with the host may be used. Examples of suitable plasmid vectors may include pBR322, pUC118, pUC119 and the like; suitable phage or bacteriophage vectors may include γgt10, γgt11 and the like; and suitable virus vectors may include pMAM-neo, pKRC and the like. Preferably, the selected vector of the present invention has the capacity to replicate in the selected host cell.

Recognized prokaryotic hosts include bacteria such as *E. coli*, Bacillus, Streptomyces, Pseudomonas, Salmonella, Serratia, and the like. However, under such conditions, the peptide will not be glycosylated. The prokaryotic host must be compatible with the replicon and control sequences in the expression plasmid.

To express TKA-1 (or a functional derivative thereof) in a prokaryotic cell, it is necessary to operably link the TKA-1 sequence to a functional prokaryotic promoter. Such promoters may be either constitutive or, more preferably, regulatable (i.e., inducible or derepressible). Examples of constitutive promoters include the int promoter of bacteriophage λ, the bla promoter of the β-lactamase gene sequence of pBR322, and the CAT promoter of the chloramphenicol acetyl transferase gene sequence of pPR325, and the like. Examples of inducible prokaryotic promoters include the major right and left promoters of bacteriophage λ ($P_L$ and $P_R$), the trp, recA, λacZ, λacI, and gal promoters of *E. coli*, the α-amylase (Ulmanen et at., *J. Bacteriol.* 162:176–182 (1985)) and the C-28-specific promoters of B. subtilis (Gilman et at., Gene sequence 32:11–20 (1984)), the promoters of the bacteriophages of Bacillus (Gryczan, In: The Molecular Biology of the Bacilli, Academic Press, Inc., NY (1982)), and Streptomyces promoters (Ward et at., *Mol. Gen. Genet.* 203:468–478 (1986)). Prokaryotic promoters are reviewed by Glick (*J. Ind. Microbiot.* 1:277–282 (1987)); Cenatiempo (*Biochimie* 68:505–516 (1986)); and Gottesman (*Ann. Rev. Genet.* 18:415–442 (1984)).

Proper expression in a prokaryotic cell also requires the presence of a ribosome binding site upstream of the gene sequence-encoding sequence. Such ribosome binding sites are disclosed, for example, by Gold et at. (*Ann. Rev. Microbiol.* 35:365–404 (1981)). The selection of control sequences, expression vectors, transformation methods, and the like, are dependent on the type of host cell used to express the gene. As used herein, "cell", "cell line", and "cell culture" may be used interchangeably and all such designations include progeny. Thus, the words "transformants" or "transformed cells" include the primary subject cell and cultures derived therefrom, without regard to the number of transfers. It is also understood that all progeny may not be precisely identical in DNA content, due to deliberate or inadvertent mutations. However, as defined, mutant progeny have the same functionality as that of the originally transformed cell.

Host cells which may be used in the expression systems of the present invention are not strictly limited, provided that they are suitable for use in the expression of the TKA-1 peptide of interest. Suitable hosts may often include eukaryotic cells. Preferred eukaryotic hosts include, for example, yeast, fungi, insect cells, mammalian cells either in vivo, or in tissue culture. Mammalian cells which may be useful as hosts include HeLa cells, cells of fibroblast origin such as VERO or CHO-K1, or cells of lymphoid origin and their derivatives. Preferred mammalian host cells include SP2/0 and J558L, as well as neuroblastoma cell lines such as IMR 332 which may provide better capacities for correct post-translational processing.

In addition, plant cells are also available as hosts, and control sequences compatible with plant cells are available, such as the cauliflower mosaic virus 35S and 19S, and nopaline synthase promoter and polyadenylation signal sequences. Another preferred host is an insect cell, for example the Drosophila larvae. Using insect cells as hosts, the Drosophila alcohol dehydrogenase promoter can be used. Rubin, *Science* 240:1453–1459 (1988). Alternatively, baculovirus vectors can be engineered to express large amounts of TKA-1 in insects cells (Jasny, *Science* 238:1653 (1987); Miller et al., In: Genetic Engineering (1986), Setlow, J. K., et al., eds., Plenum, Vol. 8, pp. 277–297).

Any of a series of yeast gene sequence expression systems can be utilized which incorporate promoter and termination elements from the actively expressed gene sequences coding for glycolytic enzymes are produced in large quantities when yeast are grown in mediums rich in glucose. Known glycolytic gene sequences can also provide very efficient transcriptional control signals. Yeast provides substantial advantages in that it can also carry out post-translational peptide modifications. A number of recombinant DNA strategies exist which utilize strong promoter sequences and high copy number of plasmids which can be utilized for production of the desired proteins in yeast. Yeast recognizes leader sequences on cloned mammalian gene sequence products and secretes peptides bearing leader sequences (i.e., pre-peptides). For a mammalian host, several possible vector systems are available for the expression of TKA-1.

A wide variety of transcriptional and translational regulatory sequences may be employed, depending upon the nature of the host. The transcriptional and translational regulatory signals may be derived from viral sources, such as adenovirus, bovine papilloma virus, cytomegalovirus, simian virus, or the like, where the regulatory signals are associated with a particular gene sequence which has a high level of expression. Alternatively, promoters from mammalian expression products, such as actin, collagen, myosin, and the like, may be employed. Transcriptional initiation regulatory signals may be selected which allow for repression or activation, so that expression of the gene sequences can be modulated. Of interest are regulatory signals which are temperature-sensitive so that by varying the temperature, expression can be repressed or initiated, or are subject to chemical (such as metabolite) regulation.

Expression of TKA-1 in eukaryotic hosts requires the use of eukaryotic regulatory regions. Such regions will, in general, include a promoter region sufficient to direct the initiation of RNA synthesis. Preferred eukaryotic promoters include, for example, the promoter of the mouse metallothionein I gene sequence (Hamer et al., *J. Mol. Appl. Gen.* 1:273–288 (1982)); the TK promoter of Herpes virus (McKnight, *Cell* 31:355–365 (1982)); the SV40 early promoter (Benoist et al., *Nature* (London) 290:304–310 (1981)); the yeast gal4 gene sequence promoter (Johnston et al., *Proc. Natl. Acad. Sci.* (USA) 79:6971–6975 (1982); Silver et al., *Proc. Natl. Acad. Sci.* (USA) 81:5951–5955 (1984)).

Translation of eukaryotic mRNA is initiated at the codon which encodes the first methionine. For this reason, it is preferable to ensure that the linkage between a eukaryotic promoter and a DNA sequence which encodes TKA-1 (or a functional derivative thereof) does not contain any intervening codons which are capable of encoding a methionine (i.e., AUG). The presence of such codons results either in a formation of a fusion protein (if the AUG codon is in the same reading frame as the TKA-1 coding sequence) or a frame-shift mutation (if the AUG codon is not in the same reading frame as the TKA-1 coding sequence).

A TKA-1 nucleic acid molecule and an operably linked promoter may be introduced into a recipient prokaryotic or eukaryotic cell either as a nonreplicating DNA (or RNA) molecule, which may either be a linear molecule or, more preferably, a closed covalent circular molecule. Since such molecules are incapable of autonomous replication, the expression of the gene may occur through the transient expression of the introduced sequence. Alternatively, permanent expression may occur through the integration of the introduced DNA sequence into the host chromosome.

A vector may be employed which is capable of integrating the desired gene sequences into the host cell chromosome. Cells which have stably integrated the introduced DNA into their chromosomes can be selected by also introducing one or more markers which allow for selection of host cells which contain the expression vector. The marker may provide for prototrophy to an auxotrophic host, biocide resistance, e.g., antibiotics, or heavy metals, such as copper, or the like. The selectable marker gene sequence can either be directly linked to the DNA gene sequences to be expressed, or introduced into the same cell by co-transfection. Additional elements may also be needed for optimal synthesis of single chain binding protein mRNA. These elements may include splice signals, as well as transcription promoters, enhancers, and termination signals. cDNA expression vectors incorporating such elements include those described by Okayama, *Molec. Cell. Biol.* 3:280(1983).

The introduced nucleic acid molecule can be incorporated into a plasmid or viral vector capable of autonomous replication in the recipient host. Any of a wide variety of vectors may be employed for this purpose. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Preferred prokaryotic vectors include plasmids such as those capable of replication in *E. coil* (such as, for example, pBR322, ColE1, pSC101, PACYC 184, IIVX. Such plasmids are, for example, disclosed by Sambrook (cf. "Molecular Cloning: A Laboratory Manual", second edition, edited by Sambrook, Fritsch, & Maniatis, Cold Spring Harbor Laboratory, (1989)). Bacillus plasmids include pC194, pC221, pT127, and the like. Such plasmids are disclosed by Gryczan (In: The Molecular Biology of the Bacilli, Academic Press, NY (1982), pp. 307–329). Suitable Streptomyces plasmids include pIJ101 (Kendall et al., *J. Bacteriol.* 169:4177–4183 (1987)), and streptomyces bacteriophages such as φC31 (Chater et al., In: Sixth International Symposium on Actinomycetales Biology, Akademiai Kaido, Budapest, Hungary (1986), pp. 45–54). Pseudomonas plasmids are reviewed by John et al. (*Rev. Infect. Dis.* 8:693–704 (1986)), and Izaki (*Jpn. J. Bacteriol.* 33:729–742 (1978)).

Preferred eukaryotic plasmids include, for example, BPV, vaccinia, SV40, 2-micron circle, and the like, or their derivatives. Such plasmids are well known in the art (Botstein et al., *Miami Wntr. Symp.* 19:265–274 (1982); Broach, In: "The Molecular Biology of the Yeast Saccharomyces: Life Cycle and Inheritance", Cold Spring Harbor Laboratory, Cold Spring Harbor, N.Y., p. 445–470 (1981); Broach, *Cell* 28:203–204 (1982); Bollon et at., *J. Clin. Hematol. Oncol.* 10:39–48 (1980); Maniatis, In: Cell Biology: A Comprehensive Treatise, Vol. 3, Gene Sequence Expression, Academic Press, NY, pp. 563–608 (1980).

Once the vector or nucleic acid molecule containing the construct(s) has been prepared for expression, the DNA construct(s) may be introduced into an appropriate host cell by any of a variety of suitable means, i.e., transformation, transfection, conjugation, protoplast fusion, electroporation, particle gun technology, calcium phosphate-precipitation, direct microinjection, and the like. After the introduction of the vector, recipient cells are grown in a selective medium, which selects for the growth of vector-containing cells. Expression of the cloned gene molecule(s) results in the production of TKA-1 or fragments thereof. This can take place in the transformed cells as such, or following the induction of these cells to differentiate (for example, by administration of bromodeoxyuracil to neuroblastoma cells or the like). A variety of incubation conditions can be used to form the peptide of the present invention. The most preferred conditions are those which mimic physiological conditions.

VII. Purified TKA-1 Polypeptides

A variety of methodologies known in the art can be utilized to obtain the peptide of the present invention. The peptide may be purified from tissues or cells which naturally produce the peptide. Alternatively, the above-described isolated nucleic acid fragments could be used to express the TKA-1 protein in any organism. The samples of the present invention include cells, protein extracts or membrane extracts of cells, or biological fluids. The sample will vary based on the assay format, the detection method and the nature of the tissues, cells or extracts used as the sample.

Any eukaryotic organism can be used as a source for the peptide of the invention, as long as the source organism naturally contains such a peptide. As used herein, "source organism" refers to the original organism from which the amino acid sequence of the subunit is derived, regardless of the organism the subunit is expressed in and ultimately isolated from.

One skilled in the art can readily follow known methods for isolating proteins in order to obtain the peptide free of natural contaminants. These include, but are not limited to: size-exclusion chromatography, HPLC, ion-exchange chromatography, and immuno-affinity chromatography.

VIII. An Antibody Having Binding Affinity To A TKA-1 Polypeptide And A Hybridoma Containing the Antibody.

The present invention relates to an antibody having binding affinity to a TKA-1 polypeptide. The polypeptide may have the amino acid sequence set forth in FIG. 1A–4F (SEQ ID NO:2), or functional derivative thereof, or at least 9 contiguous amino acids thereof (preferably, at least 20, 30, 35, or 40 contiguous amino acids thereof).

The present invention also relates to an antibody having specific binding affinity to an TKA-1 polypeptide. Such an antibody may be isolated by comparing its binding affinity to a TKA-1 polypeptide with its binding affinity to another polypeptide. Those which bind selectively to TKA-1 would be chosen for use in methods requiring a distinction between TKA-1 and other polypeptides. Such methods could include, but should not be limited to, the analysis of altered TKA-1 expression in tissue containing other polypeptides.

The TKA-1 proteins of the present invention can be used in a variety of procedures and methods, such as for the generation of antibodies, for use in identifying pharmaceutical compositions, and for studying DNA/protein interaction.

The TKA-1 peptide of the present invention can be used to produce antibodies or hybridomas. One skilled in the art will recognize that if an antibody is desired, such a peptide would be generated as described herein and used as an immunogen. The antibodies of the present invention include monoclonal and polyclonal antibodies, as well fragments of these antibodies, and humanized forms. Humanized forms of the antibodies of the present invention may be generated using one of the procedures known in the art such as chimerization or CDR grafting. The present invention also relates to a hybridoma which produces the above-described monoclonal antibody, or binding fragment thereof. A hybridoma is an immortalized cell line which is capable of secreting a specific monoclonal antibody.

In general, techniques for preparing monoclonal antibodies and hybridomas are well known in the art (Campbell, "Monoclonal Antibody Technology: Laboratory Techniques in Biochemistry and Molecular Biology," Elsevier Science Publishers, Amsterdam, The Netherlands (1984); St. Groth et al., *J. Immunol. Methods* 35:1–21 (1980)). Any animal (mouse, rabbit, and the like) which is known to produce antibodies can be immunized with the selected polypeptide. Methods for immunization are well known in the art. Such methods include subcutaneous or intraperitoneal injection of the polypeptide. One skilled in the art will recognize that the amount of polypeptide used for immunization will vary based on the animal which is immunized, the antigenicity of the polypeptide and the site of injection.

The polypeptide may be modified or administered in an adjuvant in order to increase the peptide antigenicity. Methods of increasing the antigenicity of a polypeptide are well known in the art. Such procedures include coupling the antigen with a heterologous protein (such as globulin or β-galactosidase) or through the inclusion of an adjuvant during immunization.

For monoclonal antibodies, spleen cells from the immunized animals are removed, fused with myeloma cells, such as SP2/0-Ag14 myeloma cells, and allowed to become monoclonal antibody producing hybridoma cells. Any one of a number of methods well known in the art can be used to identify the hybridoma cell which produces an antibody with the desired characteristics. These include screening the hybridomas with an ELISA assay, western blot analysis, or radioimmunoassay (Lutz et al., *Exp. Cell Res.* 175:109–124 (1988)). Hybridomas secreting the desired antibodies are cloned and the class and subclass is determined using procedures known in the art (Campbell, "Monoclonal Antibody Technology: Laboratory Techniques in Biochemistry and Molecular Biology", supra (1984)).

For polyclonal antibodies, antibody containing antisera is isolated from the immunized animal and is screened for the presence of antibodies with the desired specificity using one of the above-described procedures. The above-described antibodies may be detectably labeled. Antibodies can be detectably labeled through the use of radioisotopes, affinity labels (such as biotin, avidin, and the like), enzymatic labels (such as horse radish peroxidase, alkaline phosphatase, and the like) fluorescent labels (such as FITC or rhodamine, and the like), paramagnetic atoms, and the like. Procedures for accomplishing such labeling are well-known in the art, for example, see (Sternberger et al., *J. Histochem. Cytochem.* 18:315 (1970); Bayer et at., *Meth. Enzym. 62:308* (1979); Engval et al., *Immunot.* 109:129 (1972); Goding, *J. Immunol. Meth.* 13:215 (1976)). The labeled antibodies of the present invention can be used for in vitro, in vivo, and in situ assays to identify cells or tissues which express a specific peptide.

The above-described antibodies may also be immobilized on a solid support. Examples of such solid supports include plastics such as polycarbonate, complex carbohydrates such as agarose and sepharose, acrylic resins and such as polyacrylamide and latex beads. Techniques for coupling antibodies to such solid supports are well known in the art (Weir et al., "Handbook of Experimental Immunology" 4th Ed., Blackwell Scientific Publications, Oxford, England, Chapter 10 (1986); Jacoby et al., *Meth. Enzym.* 34, Academic Press, N.Y. (1974)). The immobilized antibodies of the present invention can be used for in vitro, in vivo, and in situ assays as well as in immunochromotography.

Furthermore, one skilled in the art can readily adapt currently available procedures, as well as the techniques, methods and kits disclosed above with regard to antibodies, to generate peptides capable of binding to a specific peptide sequence in order to generate rationally designed antipeptide peptides, for example see Hurby et al., "Application of Synthetic Peptides: Antisense Peptides", In Synthetic Peptides, A User's Guide, W. H. Freeman, NY, pp. 289–307 (1992), and Kaspczak et al., Biochemistry 28:9230–8 (1989).

Anti-peptide peptides can be generated by replacing the basic amino acid residues found in the TKA-1 peptide sequence with acidic residues, while maintaining hydrophobic and uncharged polar groups. For example, lysine, arginine, and/or histidine residues are replaced with aspartic acid or glutamic acid and glutamic acid residues are replaced by lysine, arginine or histidine.

IX. An Antibody Based Method And Kit For Detecting TKA-1.

The present invention encompasses a method of detecting an TKA-1 polypeptide in a sample, comprising: a) contacting the sample with an above-described antibody, under conditions such that immunocomplexes form, and b) detecting the presence of said antibody bound to the polypeptide. In detail, the methods comprise incubating a test sample with one or more of the antibodies of the present invention and assaying whether the antibody binds to the test sample. Altered levels of TKA-1 in a sample as compared to normal levels may indicate disease.

Conditions for incubating an antibody with a test sample vary. Incubation conditions depend on the format employed in the assay, the detection methods employed, and the type and nature of the antibody used in the assay. One skilled in the art will recognize that any one of the commonly available immunological assay formats (such as radioimmunoassays, enzyme-linked immunosorbent assays, diffusion based Ouchterlony, or rocket immunofluorescent assays) can readily be adapted to employ the antibodies of the present invention. Examples of such assays can be found in Chard, "An Introduction to Radioimmunoassay and Related Techniques" Elsevier Science Publishers, Amsterdam, The Netherlands (1986); Bullock et al., "Techniques in Immunocytochemistry," Academic Press, Orlando, FL Vol. 1 (1982), Vol. 2 (1983), Vol. 3 (1985); Tijssen, "Practice and Theory of Enzyme Immunoassays: Laboratory Techniques in Biochemistry and Molecular Biology," Elsevier Science Publishers, Amsterdam, The Netherlands (1985).

The immunological assay test samples of the present invention include cells, protein or membrane extracts of cells, or biological fluids such as blood, serum, plasma, or urine. The test sample used in the above-described method will vary based on the assay format, nature of the detection method and the tissues, cells or extracts used as the sample to be assayed. Methods for preparing protein extracts or membrane extracts of cells are well known in the art and can be readily be adapted in order to obtain a sample which is capable with the system utilized.

A kit contains all the necessary reagents to carry out the previously described methods of detection. The kit may comprise: i) a first container means containing an above-described antibody, and ii) second container means containing a conjugate comprising a binding partner of the antibody and a label. In another preferred embodiment, the kit further comprises one or more other containers comprising one or more of the following: wash reagents and reagents capable of detecting the presence of bound antibodies.

Examples of detection reagents include, but are not limited to, labeled secondary antibodies, or in the alternative, if the primary antibody is labeled, the chromophoric, enzymatic, or antibody binding reagents which are capable of reacting with the labeled antibody. The compartmentalized kit may be as described above for nucleic acid probe kits. One skilled in the art will readily recognize that the antibodies described in the present invention can readily be incorporated into one of the established kit formats which are well known in the art.

X. Isolation of Compounds Which Interact With TKA-1.

The present invention also relates to a method of detecting a compound capable of binding to a TKA-1 polypeptide comprising incubating the compound with TKA-1 and detecting the presence of the compound bound to TKA-1. The compound may be present within a complex mixture, for example, serum, body fluid, or cell extracts.

The present invention also relates to a method of detecting an agonist or antagonist of TKA-1 activity or TKA-1 binding partner activity comprising incubating cells that produce TKA-1 in the presence of a compound and detecting changes in the level of TKA-1 activity or TKA-1 binding partner activity. The compounds thus identified would produce a change in activity indicative of the presence of the compound. The compound may be present within a complex mixture, for example, serum, body fluid, or cell extracts. Once the compound is identified it can be isolated using techniques well known in the art.

The present invention also encompasses a method of agonizing (stimulating) or antagonizing TKA-1 associated activity in a mammal comprising administering to said mammal an agonist or antagonist to TKA-1 in an amount sufficient to effect said agonism or antagonism. A method of treating diseases in a mammal with an agonist or antagonist of TKA-1 related activity comprising administering the agonist or antagonist to a mammal in an amount sufficient to agonize or antagonize TKA-1 associated functions is also encompassed in the present application.

XI. Transgenic Animals.

A variety of methods are available for the production of transgenic animals associated with this invention. DNA can be injected into the pronucleus of a fertilized egg before fusion of the male and female pronuclei, or injected into the nucleus of an embryonic cell (e.g., the nucleus of a two-cell embryo) following the initiation of cell division (Brinster et al., Proc. Nat. Acad. Sci. USA 82: 4438–4442 (1985)). Embryos can be infected with viruses, especially retroviruses, modified to carry inorganic-ion receptor nucleotide sequences of the invention.

Pluripotent stem cells derived from the inner cell mass of the embryo and stabilized in culture can be manipulated in culture to incorporate nucleotide sequences of the invention. A transgenic animal can be produced from such cells through implantation into a blastocyst that is implanted into a foster mother and allowed to come to term. Animals suitable for transgenic experiments can be obtained from standard commercial sources such as Charles River (Wilmington, Mass.), Taconic (Germantown, N.Y.), Harlan Sprague Dawley (Indianapolis, Ind.), etc.

The procedures for manipulation of the rodent embryo and for microinjection of DNA into the pronucleus of the zygote are well known to those of ordinary skill in the art (Hogan et al., supra). Microinjection procedures for fish, amphibian eggs and birds are detailed in Houdebine and Chourrout, *Experientia* 47: 897–905 (1991). Other procedures for introduction of DNA into tissues of animals are described in U.S. Pat. No., 4,945,050 (Sandford et al., Jul. 30, 1990).

By way of example only, to prepare a transgenic mouse, female mice are induced to superovulate. Females are placed with males, and the mated females are sacrificed by $CO_2$ asphyxiation or cervical dislocation and embryos are recovered from excised oviducts. Surrounding cumulus cells are removed. Pronuclear embryos are then washed and stored until the time of injection. Randomly cycling adult female mice are paired with vasectomized males. Recipient females are mated at the same time as donor females. Embryos then are transferred surgically. The procedure for generating transgenic rats is similar to that of mice. See Hammer et al., *Cell* 63:1099–1112 (1990).

Methods for the culturing of embryonic stem (ES) cells and the subsequent production of transgenic animals by the introduction of DNA into ES cells using methods such as electroporation, calcium phosphate/DNA precipitation and direct injection also are well known to those of ordinary skill in the art. See, for example, *Teratocarcinomas and Embryonic Stem Cells. A Practical Approach*, E. J. Robertson, ed., IRL Press (1987).

In cases involving random gene integration, a clone containing the sequence(s) of the invention is co-transfected with a gene encoding resistance. Alternatively, the gene encoding neomycin resistance is physically linked to the sequence(s) of the invention. Transfection and isolation of desired clones are carried out by any one of several methods well known to those of ordinary skill in the art (E. J. Robertson, supra).

DNA molecules introduced into ES cells can also be integrated into the chromosome through the process of homologous recombination. Capecchi, *Science* 244: 1288–1292 (1989). Methods for positive selection of the recombination event (i.e., neo resistance) and dual positive-negative selection (i.e., neo resistance and gancyclovir resistance) and the subsequent identification of the desired clones by PCR have been described by Capecchi, supra and Joyner et al., *Nature* 338: 153–156 (1989), the teachings of which are incorporated herein. The final phase of the procedure is to inject targeted ES cells into blastocysts and to transfer the blastocysts into pseudopregnant females. The resulting chimeric animals are bred and the offspring are analyzed by Southern blotting to identify individuals that carry the transgene. Procedures for the production of non-rodent mammals and other animals have been discussed by others. See Houdebine and Chourrout, supra; Pursel et al., *Science* 244:1281–1288 (1989); and Simms et al., *Bio/Technology* 6:179–183 (1988).

Thus, the invention provides transgenic, nonhuman mammals containing a transgene encoding a TKA-1 polypeptide or a gene effecting the expression of a TKA-1 1 polypeptide. Such transgenic nonhuman mammals are particularly useful as an in vivo test system for studying the effects of introducing a TKA-1 polypeptide, regulating the expression of a TKA-1 polypeptide (i.e., through the introduction of additional genes, antisense nucleic acids, or ribozymes).

A "transgenic animal" is an animal having cells that contain DNA which has been artificially inserted into a cell, which DNA becomes part of the genome of the animal which develops from that cell. Preferred transgenic animals are primates, mice, rats, cows, pigs, horses, goats, sheep, dogs and cats. The transgenic DNA may encode for a human TKA-1 polypeptide. Native expression in an animal may be reduced by providing an amount of anti-sense RNA or DNA effective to reduce expression of the receptor.

XII. Gene Therapy

TKA-1 or its genetic sequences will also be useful in gene therapy (reviewed in Miller, *Nature* 357:455–460, (1992). Miller states that advances have resulted in practical approaches to human gene therapy that have demonstrated positive initial results. The basic science of gene therapy is described in Mulligan, *Science* 260:926–931, (1993).

In one preferred embodiment, an expression vector containing the TKA-1 coding sequence is inserted into cells, the cells are grown in vitro and then infused in large numbers into patients. In another preferred embodiment, a DNA segment containing a promoter of choice (for example a strong promoter) is transferred into cells containing an endogenous TKA-1 in such a manner that the promoter segment enhances expression of the endogenous TKA-1 gene (for example, the promoter segment is transferred to the cell such that it becomes directly linked to the endogenous TKA-1 gene).

The gene therapy may involve the use of an adenovirus containing TKA-1 cDNA targeted to a tumor, systemic TKA-1 increase by implantation of engineered cells, injection with TKA-1 virus, or injection of naked TKA-1 DNA into appropriate tissues.

Target cell populations may be modified by introducing altered forms of one or more components of the protein complexes in order to modulate the activity of such complexes. For example, by reducing or inhibiting a complex component activity within target cells, an abnormal signal transduction event(s) leading to a condition may be decreased, inhibited, or reversed. Deletion or missense mutants of a component, that retain the ability to interact with other components of the protein complexes but cannot function in signal transduction may be used to inhibit an abnormal, deleterious signal transduction event.

Expression vectors derived from viruses such as retroviruses, vaccinia virus, adenovirus, adeno-associated virus, herpes viruses, several RNA viruses, or bovine papilloma virus, may be used for delivery of nucleotide sequences (e.g., cDNA) encoding recombinant TKA-1 protein into the targeted cell population (e.g., tumor cells). Methods which are well known to those skilled in the art can be used to construct recombinant viral vectors containing coding sequences. See, for example, the techniques described in Maniatis et al., *Molecular Cloning: A Laboratory Manual*, Cold Spring Harbor Laboratory, N.Y. (1989), and in Ausubel et al., *Current Protocols in Molecular Biology*, Greene Publishing Associates and Wiley Interscience, N.Y. (1989). Alternatively, recombinant nucleic acid molecules encoding protein sequences can be used as naked DNA or in reconstituted system e.g., liposomes or other lipid systems for delivery to target cells (See e.g., Felgner et al., *Nature* 337:387–8, 1989). Several other methods for the direct transfer of plasmid DNA into cells exist for use in human gene therapy and involve targeting the DNA to receptors on cells by complexing the plasmid DNA to proteins. See, Miller, supra.

In its simplest form, gene transfer can be performed by simply injecting minute amounts of DNA into the nucleus of a cell, through a process of microinjection, Capecchi MR, *Cell* 22:479–88 (1980). Once recombinant genes are introduced into a cell, they can be recognized by the cells normal mechanisms for transcription and translation, and a gene product will be expressed. Other methods have also been attempted for introducing DNA into larger numbers of cells. These methods include: transfection, wherein DNA is precipitated with $CaPO_4$ and taken into cells by pinocytosis (Chen C. and Okayama H, *Mol. Cell Biol.* 7:2745–52

(1987)); electroporation, wherein cells are exposed to large voltage pulses to introduce holes into the membrane (Chu G. et al., Nucleic Acids Res., 15:1311–26 (1987)); lipofection/ liposome fusion, wherein DNA is packaged into lipophilic vesicles which fuse with a target cell (Felgner PL., et al., Proc. Natl. Acad. Sci. USA. 84:7413–7 (1987)); and particle bombardment using DNA bound to small projectiles (Yang NS. et al., Proc. Natl. Acad. Sci. 87:9568–72 (1990)). Another method for introducing DNA into cells is to couple the DNA to chemically modified proteins.

It has also been shown that adenovirus proteins are capable of destabilizing endosomes and enhancing the uptake of DNA into cells. The admixture of adenovirus to solutions containing DNA complexes, or the binding of DNA to polylysine covalently attached to adenovirus using protein crosslinking agents substantially improves the uptake and expression of the recombinant gene. Curiel DT et al., Am. J. Respir. Cell. Mol. Biol., 6:247–52 (1992).

As used herein "gene transfer" means the process of introducing a foreign nucleic acid molecule into a cell. Gene transfer is commonly performed to enable the expression of a particular product encoded by the gene. The product may include a protein, polypeptide, anti-sense DNA or RNA, or enzymatically active RNA. Gene transfer can be performed in cultured cells or by direct administration into animals. Generally gene transfer involves the process of nucleic acid contact with a target cell by non-specific or receptor mediated interactions, uptake of nucleic acid into the cell through the membrane or by endocytosis, and release of nucleic acid into the cytoplasm from the plasma membrane or endosome. Expression may require, in addition, movement of the nucleic acid into the nucleus of the cell and binding to appropriate nuclear factors for transcription.

As used herein "gene therapy" is a form of gene transfer and is included within the definition of gene transfer as used herein and specifically refers to gene transfer to express a therapeutic product from a cell in vivo or in vitro. Gene transfer can be performed ex vivo on cells which are then transplanted into a patient, or can be performed by direct administration of the nucleic acid or nucleic acid-protein complex into the patient.

In another preferred embodiment, a vector having nucleic acid sequences encoding a TKA-1 is provided in which the nucleic acid sequence is expressed only in specific tissue. Methods of achieving tissue-specific gene expression as set forth in International Publication No. WO 93/09236, filed Nov. 3, 1992 and published May 13, 1993.

In all of the preceding vectors set forth above, a further aspect of the invention is that the nucleic acid sequence contained in the vector may include additions, deletions or modifications to some or all of the sequence of the nucleic acid, as defined above.

In another preferred embodiment, a method of gene replacement is set forth. "Gene replacement" as used herein means supplying a nucleic acid sequence which is capable of being expressed in vivo in an animal and thereby providing or augmenting the function of an endogenous gene which is missing or defective in the animal.

EXAMPLES

The examples below are non-limiting and are merely representative of various aspects and features of the present invention. The examples below demonstrate the isolation, and characterization of the novel tyrosine kinase associated protein, TKA-1.
Material and Methods
Isolation and labelling of the EGF-PDGF-receptor chimera A chimeric receptor consisting of the extracellular and transmembrane domains of the EGF receptor and the cytoplasmic deomain of the PDGF-receptor (EP-R) was purified from 293 cells that were transiently transfected with a cytomegalovirus (CMV) promoter-driven EP-R expression plasmid by immunoprecipitation using protein A and monoclonal antibody (MAb) 108.1 (Honegger, A. M. et al., (1989), Proc. Natl. Acad. Sci. USA, 86, 925–929). The immune complex was washed three times with HNTG-buffer (20 mM HEPES, pH 7.5, 150 mM NaCl, 10% glycerol) containing 0.1% Triton X-100 and subsequently with kinase-buffer (20 mM HEPES, pH 7.5, 1 mM MnCl$_2$ 10% glycerol). Labelling of the receptor was carried out in 50 ml of kinase buffer containing 100 mCi $^{32}P_g$ATP at room temperature on a shaker for 40 minutes. Subsequently, cold ATP was added (2.5 ml of a 1 mM solution) and the incubation was continued for another 10 minutes. Unincorporated ATP was removed by washing three times with HNTG buffer. After the immune complex was disrupted by incubation in 0.2M glycine, pH 2.5, the protein A sepharose was removed by centrifugation and the supernatant neutralized with 1M Tris-HCl, pH 8.8.
Screening of λgtII expression library A λgtII library constructed from human placenta mRNA (Clontech) was plated at a density of 5×10$^4$ plaques per 150 mm agar plate. A total of 5×10$^5$ plaques were initially screened. After incubation of the plates for 4 hours at 42° C., isopplates were overlaid with isopropyl-b-D-thiogalactopyranoside (IPTG) impregnated filters, as described by Macgregor, P. F. et al., (1990), Oncogene, 5, 451–458. Incubation was continued overnight at 37° C. The filters were removed, washed several times with TBST buffer (10 mM Tris-HCl pH 8.0, 150 mM NaCl, 0.05% Triton X-100), and subsequently incubated in TBST containing 5% Carnation dry milk for 4 hours at 4° C. Then in vitro tyrosine-phosphorylated receptor was added (~1×10$^6$ cpm/ml) and incubation continued overnight. The filters were washed 5 times at room temperature in phosphate-buffered saline containing 0.2% Triton X-100. Filters were dried and exposed to X-ray film at −80° C. Positive plaques were enriched by sequential screenings and the CDNA insert was sequenced after subcloning into Bluescript.
Expression vector construction and generation of stable cell transfectants The chimeric receptor EP-R, EP-R deletion mutants, HER1-2, and EK-R, are described elsewhere (Seedorf, K. et al., (1991), J. Biol. Chem., 266, 12424–12431; Seedorf, K. et al., (1992), Mol. Cell. Biol., 12, 4347–4356; Lee, J et al., (1989), EMBO J., 8, 167–173; Herbst, R. et al., (1991), J. Biol. Chem., 266,19908–19916). The TKA-1 cDNA was cloned via EcoRI into a CMV promoter-driven expression vector for transient expression in 293 cells. For the generation of stably expressing NIH3T3 cells, TKA-1 cDNA was cloned via the same restriction site into pLEN. Ecotrophic recombinant retrovirus stocks were prepared from the helper virus-free producer line GP+E-86 (Markovitz et al., 1988). Low-titer amphotrophic virus, which was generated by transient transfection of retrovirus expression plasmids into the helper virus-free packaging cell line PA 317 (Miller, A. D. et al., (1985), Mol. Cell. Biol., 5, 431–437), was used to infect GP+E-86 secondary packaging cells, followed by selection of GP+E-86 producer cells in G418 (1 mg/ml). The virus titer was determined by infection of NIH3T3 cells with serial dilutions and determination of G418-resistant colonies. The titers were between 2 and 5×10$^5$. For retrovirus-mediated gene transfer, subconfluent NIH3T3 cells (10$^5$ cells per 6-cm dish) were incubated with supernatants of GP+E-86 producer cells in the presence of Polybrene (4 mg/ml; Aldrich) overnight, followed by selection with G418. Stable expression of TKA-1 was determined by Western blot analysis using TKA-1 -specific antibodies.

Transfections and immunoprecipitation

Polyclonal antibodies against TKA-1 were produced by immunizing rabbits with a glutathione-S-transferase fusion protein containing the entire coding region of TKA-1 expressed in *E. coli*. The EGF-R and EP-R chimera were precipitated with MAb 108.1. For detection in Western blots, a polyclonal antisera directed against the extracellular domain of the EGF-R was used. The PDGF-β-R was precipitated using antisera B2 (Ronnstrand et al., *JBC* 263 (21):10429–10425, 1988) and monoclonal antibody 28D4C10 (kindly provided by H. J. Bühring et al, *Leukemia* 5 (10):854–860, 1991).

High efficiency transfection of human kidney fibroblasts (293 cells) was essentially performed as described by Chen, C. and Okayama, H. (1987), *Mol. Cell. Biol,* 7, 2745–2752 and Gorman, C. M. et al., (1989), *Virology,* 171, 377–385. For labeling, medium was replaced by methionine free DMEM containing 0.5% FCS and 60 mCi [$^{35}$S] methionine/ml. Cells were treated with ligand and lysed as described by Kris, R. M et al., (1985), *Cell,* 40, 619–625. Immunoprecipitates were separated on 7.5% PAA gels, transferred to nitrocellulose and incubated with a mouse monoclonal antibody directed against phosphotyrosine (5E2; Fendly, B. M. et al., (1990), *Cancer Res.,* 50, 1550–1558), TKA-1, and EGF-R, respectively. Protein bands were made visible using horseradish peroxidase-coupled goat anti-mouse and goat anti-rabbit antibodies and the ECL (Amersham) detection method.

Northern blot analysis

Poly (A)$^+$ RNA was prepared from human tissue or tumor cell lines as described by Sambrook et al. (1989). For Northern analysis, 3 mg RNA were size-fractionated by electrophoresis in a 1.2% agarose-2.2M formaldehyde gel, transferred to a nitrocellulose membrane and backed at 80° C. for 2 hours. Following prehybridization, the blot was hybridized with a $^{32}$P-labelled TKA-1 probe. Hybridization was carried out overnight at 42° C. in the presence of 50% formamide, 5×SSC, 0.1% SDS, and 5×Denhardt's solution. The membrane was then washed in 0.1×SSC, 0.1% SDS at 42° C. and exposed to X-ray film at −80° C. for 48 hours using an intensifying screen.

Thymidine incorporation assay

Cells ($10^5$ per well) were seeded into 24-well dishes pretreated with 0.2% gelatin. Cells were grown for 3 days in DMEM containing 10% FCS and then starved for 48 hours in 0.5% FCS. PDGF was added for 18 hours and subsequently [$^3$H] thymidine (0.5 mCi/well) for 4 hours. The cells were washed three times with PBS and incubated with ice cold 10% trichloroacetic acid (TCA) for 30 minutes. After washing twice with the same solution, the TCA precipitate was solubilized in 0.2M NaOH, 1% SDS, neutralized, and counted in a scintillation counter.

Actin reorganization

Cells were seeded on coverslips and incubated for 24 hours in DMEM, 10% FCS and subsequently for 24 hours in DMEM, 0.5% FCS. PDGF-BB was added at a concentration of 10 ng/ml for various times, washed three times with PBS, and fixed for 20 minutes at room temperature in 3% paraformaldehyde freshly prepared in PBS. After permeabilization with −20° C. acetone for 2 minutes, cells were stained with rhodamine-conjugated phalloidin (50 mg/ml in PBS, Sigma). After washing in PBS, coverslips were mounted in PBS/glycerol 1:1 and viewed in a Zeiss fluorescence microscope.

EXAMPLE 1 cDNA isolation and characterization

To identify novel polypeptides that bind with high affinity to RTKs and may be involved in regulation or transduction of cellular signals, we followed the CORT procedure but utilized, instead of a phosphorylated receptor fragment, an entire in vitro autophosphorylated receptor in form of the RTK chimera, EP-R, which consists of extracellular EGF binding and PDGF-β receptor cytoplasmic sequences (Seedorf, K. et al., (1991), *J. Biol. Chem.,* 266, 12424–12431), as a probe on a human placental λgtll expression library. Screening of 3×$10^5$ plaques yielded 8 positive signals. The cDNA inserts of the recombinant λ phage were subcloned and partially sequenced. Seven of these proved to encode the noncatalytic subunit of PI3K, p85, which demonstrated that the experiment was successful. One clone with a cDNA insert of about 1600 bp encoded an apparently novel polypeptide, which was designated tyrosine kinase activator protein 1 (TKA-1). Protein sequence database searches yielded no match with known proteins.

To examine whether binding of the recombinant λgt11-encoded lacZ fusion protein could be reproduced in vitro, a glutathione S-transferase TKA-1 fusion protein was generated by cloning the partial TKA-1 cDNA into a PGEX bacterial expression vector. This purified glutathione S-transferase TKA-1 fusion protein was then shown to associate specifically with the immunoprecipitated EP-R chimera by immunoblot analysis using anti-glutathione S-transferase-specific antibodies.

Translation of the complete nucleotide sequence revealed an open reading frame of 450 amino acids (FIG. 1A–4F (SEQ ID NO:2). To examine whether this cDNA represented a full-length clone, we screened a λZAP cDNA library prepared from SK-BR-3 mammary carcinoma cell mRNA with a $^{32}$P-labeled 5' clone 17 fragment. Several positives were isolated and analyzed by restriction and sequence analysis. None of these clones had an extended 5' end, and one was identical to clone 17, while the others were shorter.

TKA-1 has a translation initiation codon at position 97 (ATG), flanked by nucleotides matching Kozak's criteria for a translation initiation site (Kozak, M. (1991), *J. Biol. Chem.,* 266, 19867–19870), a stop codon (TGA) at position 1447, and a polyadenylation signal sequence (AATAAA) at position 1579–1585. Sequence comparison analysis using GenBank revealed that TKA-1 contains no src homology region 2 (SH2) or 3 (SH3) domains nor has the coding sequence any striking homology with other proteins. A stretch of 106 amino acids (aa 7–112) is duplicated within the sequence (aa 146–252) with 65% identity, and a second stretch of 15 amino acids (aa 346–360 and 361–376) with 47% identity. The calculated molecular mass of the protein encoded by the longest open reading frame beginning with a methionine codon was 49,346.

EXAMPLE 2

Northern blot analysis

To determine the expression of TKA-1 mRNA in various human tissues, Northern blot analysis was performed using a DNA probe corresponding to the first 1,032 nucleotides. 3 μg of poly(A)+mRNA obtained from various human tissues (A) or mammary carcinoma cell lines (B) were separated on a 1.2% agarose-formaldehyde gel, transferred to nitrocellulose, and hybridized with a $^{32}$P-labeled, 1,031-nucleotide long TKA-1 cDNA fragment. Exposure time was 4 days at −70° C. with an intensifying screen.

Three hybridizing mRNA bands of 2.2, 1.6, and 1.4 kb were observed. The 1.6 and 1.4 kb mRNAs were found in all tissues analyzed, while the 2.2 kb mRNA was expressed in brain, liver, placenta, spleen, kidney, and duodenum, but not in muscle and stomach. Differential quantitative and qualitative expression of three TKA-1 mRNAs in several mammary carcinoma-derived cell lines suggest a functional significance. The fact that the largest mRNA expressed in SK-BR-3 cells was the 1.6 kb species supported our conclusion that our cDNA clone represented a full-length copy of this TKA-1 mRNA.

EXAMPLE 3
Expression of TKA-1 in 293

The complete TKA-1 cDNA was cloned into a CMV early promoter-driven expression vector for transient expression in 293 cells (ATCC# CRL 1573). After transfection and metabolic labeling, the cells were lysed or separated into cytosol and membrane fractions. TKA-1 was subsequently precipitated with a TKA-1 -specific antiserum and analyzed by SDS-PAGE.

In particular, 293 cells transiently transfected with TKA-1 expression plasmid were biosynthetically labeled and lysed or fractionated into soluble and membrane-bound polypeptides. TKA-1 was subsequently immunoprecipitated using TKA-1 -specific antisera from the soluble fraction, the membrane fraction, and from total cell lysates. In parallel, EP-R and TKA-1 expression plasmids were simultaneously transfected and EP-R immunoprecipitated from total cell lysates using MAb 108.1. In one lane, 293 cell lysates containing overexpressed TKA-1 were treated with MAb 108.1, while in another lane, TKA-1 was immunoprecipitated from nontransfected 293 cells. Polypeptides were separated on a 7.5% SDS-PAGE gel and exposed for 48 hours to X-ray film.

Precipitation of TKA-1 from [$^{35}$S]methionine-labeled crude cell lysates revealed two bands of 47 and 53 kD. The 53 kD protein was enriched in the soluble fraction, while the 47 kD protein, which corresponded to the predicted molecular weight, was located primarily in the membrane fraction. Simultaneous overexpression of EP-R and TKA-1 cDNA, and subsequent immunoprecipitation of EP-R with MAb 108.1 resulted in selective coprecipitation of the 47 kD TKA-1 protein, indicating that the 53 kD protein does not interact with the receptor. Transfection of the TKA-1 expression plasmid alone and subsequent immunoprecipitation with MAb 108.1 yielded no band corresponding to TKA-1, clearly demonstrating that precipitation described immediately above was mediated exclusively by the EP-R, while immunoprecipitation of TKA-1 from nontransfected 293 cells revealed a faint band of 47 kD, demonstrating that 293 cells express endogenous TKA-1. The same band was detected in immunoblots with anti-TKA-1 antiserum.

To further investigate the identity of the 47 and 53 kD bands precipitating from transiently transfected 293 cell lysates, we used total cell extracts from nontransfected 293, A172 (ATCC# CRL 1620), T47D (ATCC# HTB 133), HBL-100 (ATCC# HTB 124), MCF-7 (ATCC# GTB 22), and SK-BR-3 (ATCC# HTB 30) cells and tested for TKA-1 expression by Western blot analysis using affinity-purified TKA-1 antibodies. In all human cell lines, only the 47 kD TKA-1 form was detected, which migrated as a diffuse band of varying intensity. This suggested that transient overexpression in 293 cells resulted in a currently unknown covalent modification of a fraction of newly synthesized TKA-1.

EXAMPLE 4
TKA-1 interacts specifically with the C-terminus of the PDGF-β receptor To determine functional characteristics of TKA-1, various RTKs and RTK mutants were overexpressed with and without TKA-1. After metabolic labeling of the cells with [$^{35}$S] methionine, the receptors were immunoprecipitated with monoclonal antibody 108.1 against the EGF-R extracellular domain present in all the receptors used. Binding of TKA-1 was determined by coimmunoprecipitation of the 47 kD form.

In a first set of experiments, EP-R, CSF-1-R, and EK-R expression vectors (an EGF-R/kit chimera, Herbst, R. et al., (1991), J. Biol. Chem.., 266,19908–19916) were transfected alone or together with the TKA-1 expression plasmid into 293 fibroblasts.

In particular, 293 cells were transiently transfected with receptor expression plasmid and simultaneously with receptor and TKA-1 expression plasmids. Cells were metabolically labeled with [$^{35}$S]methionine, after which lysates were prepared and RTKs immunoprecipitated with 108.1 (EP-R and EK-R) or CSF-1 receptor-specific antibodies. The immunoprecipitated proteins were separated on a 7.5% SDS-PAGE gel. Autoradiography was performed overnight.

Only immunoprecipitation of EP-R resulted in coimmunoprecipitation of TKA-1, demonstrating that the closely related CSF-1-R and kit receptor cytoplasmic domains do not mediate binding of TKA-1. The human EGF-R (HER), HER2, and insulin cytoplasmic domains were also found to be binding-negative, indicating that TKA-1 binds specifically to the PDGF-R. In a similar experiment we found that both α and β PDGF-R interacted with similar affinity with TKA-1.

In a third set of experiments, we investigated the binding of TKA-1 to the wild type (EP-R) and various PDGF-R cytoplasmic domain deletion mutants, including EP-RD83, lacking 83 amino acids of the kinase insertion sequence, EP-RD103, lacking the entire kinase insertion sequence, and three progressive C-terminal deletion mutants lacking 74 (EP-RDCT74), 80 (EP-RDCT80), and 115 (EP-RDCT115) amino acids (Seedorf et al., 1992).

In particular, 293 cells were transiently transfected with EP-R, EP-RD83 (lacking 83 amino acids of the PDGF-R kinase insertion sequence (KIS)), EP-RD103 (lacking the entire KIS), EP-RDCT74, EP-RDCT80, and EP-RDCT115 (lacking the PDGF-R C-terminal-most 74, 80, and 115 amino acids, respectively), expression plasmid alone or together with TKA-1 expression plasmid. Cells were further treated as described in the legend to FIG. 3A. After immunoprecipitation of the receptors with MAb 108.1, the proteins were separated on a 7.5% SDS-PAGE gel and exposed to X-ray film.

The kinase insertion mutants mediated normal binding of TKA-1, while all C-terminal truncation mutants lost their ability to coimmunoprecipitate this protein. These data indicate that the C-terminal-most 74 amino acids contain the TKA-1 binding site and, because EP-RD103 is autophosphorylation-negative, that receptor autophosphorylation is not required.

EXAMPLE 5

TKA-1 activates ligand-independent receptor phosphorylation on tyrosine

A potential role in signal regulation for TKA-1 was first examined by determining the effects of TKA-1 on EP-R autophosphorylation and receptor-mediated substrate phosphorylation in transiently overexpressing 293 fibroblasts. Cells were transfected with TKA-1, EP-R, or EP-R+TKA-1, starved for 24 hours in medium containing 0.5% FCS, and subsequently left untreated or treated with EGF for 10 minutes. After lysis in SDS-containing buffer, cell proteins were separated by SDS-PAGE and transferred to nitrocellulose. Immunoblotting with antiphosphotyrosine-specific antibodies revealed strong EP-R and substrate phosphorylation upon EGF addition (exposure time was 1 minute using horseradish peroxidase coupled second antibodies and ECL (Amersham)). Coexpression of TKA-1 stimulated receptor and substrate phosphorylation in the absence of EGF, whereas EGF treatment and TKA-1 coexpression appeared to have additive effects. Expression of TKA-1 in the absence of EP-R caused no protein tyrosine phosphorylation, demonstrating that substrate phosphorylation was mediated exclusively by the activated EP-R. Expression levels of both EP-R and TKA-1 were comparable in relevant samples.

Our data indicated that TKA-1 was able to partially activate PDGF-R kinase activity by binding to receptor C-tail sequences. To extend this observation, we examined the activation of receptor-bound PI3K. 293 cells were transfected as before (i.e., untransfected, transfected with EP-R, or EP-R and TKA-1 expression plasmids) and metabolically labeled with [$^{35}$S]methionine overnight in the presence of 0.5% FCS. After stimulation with EGF for 10 minutes, EP-R was immunoprecipitated with MAb 108.1. From each immunoprecipitate, three equal aliquots were prepared to test the amounts of EP-R and coimmunoprecipitation of TKA-1, to determine the phosphotyrosine state of the receptor by immunoblotting with antiphosphotyrosine antibody, and to measure receptor-bound PI-3-kinase activity. Two sets of aliquots were separated on 7.5% SDS-PAGE gels, from which one was directly exposed to X-ray film, while the other was subjected to Western blot analysis using antiphosphotyrosine-specific antibody 5E2. The third set of aliquots was used to determine the amount of PI-3-kinase activity that coimmunoprecipitated with EP-R. The PIP spots were scraped from TLC plates and analyzed by Cerenkov counting (C−: 20 cpm, C+: 25 cpm, EP-R−: 315 cpm, EP-R+: 945 cpm, EP-R TKA-1−: 1045 cpm, EP-R TKA-1+: 1630 cpm).

Approximately equal amounts of EP-R were immunoprecipitated and that in cells that coexpressed TKA-1, immunoprecipitation of the receptor resulted in coimmunoprecipitation of TKA-1. Moreover, coexpression of TKA-1 resulted in activation of EP-R autophosphorylation in the absence of ligand and in binding of active PI3K. The extent of TKA-1 binding-induced, receptor-bound PI3K activity was almost identical to that induced by ligand activation of the receptor in the absence of TKA-1 (1045 cpm versus 945 cpm).

EXAMPLE 6
Stable expression of TKA-1 in NIH3T3 fibroblasts

For stable expression in NIH3T3 fibroblasts, the TKA-1 cDNA was cloned into an SV40 promoter-driven expression vector. After transfection and selection with G418, several clones were isolated 14 days later and TKA-1 expression was determined by Western blot analysis using TKA-1-specific antisera.

Using TKA-1-specific antibodies, several clones expressing TKA-1 at different levels were identified. The apparent molecular weight of TKA-1 expressed in NIH3T3 transfectants matched that of the endogenous protein in 293 and SK-BR-3 cells, which further confirmed that the 47 kD band of transfected 293 cells corresponds to the native form. Nontransfected NIH3T3 cells did not show a band corresponding to TKA-1, possibly due to a lack of crossreactivity of the antiserum with the mouse homolog.

In order to determine possible changes in the mitogenic response of NIH3T3/TKA-1 transfectants to PDGF, eight randomly selected clones were pooled and compared with nontransfected NIH3T3 cells. [$^3$H]thymidine incorporation into DNA was determined as described herein. Equal amounts of NIH3T3 cells and a pool of 8 randomly selected TKA-1-expressing NIH3T3 cells were incubated for 18 hours in the presence of increasing concentrations of PDGF. [$^3$H]thymidine was added for 4 hours and trichloroacetic acid-precipitable radioactivity was determined. The average of two independent experiments was used for analysis.

TKA-1-expressing NIH3T3 cells displayed enhanced sensitivity to PDGF in a $^3$H-thymidine incorporation assay. The basal level of DNA synthesis in serum-starved cells was about 3 times higher than in cells expressing TKA-1. This level was reached in NIH3T3 cells only with 2 ng/ml PDGF, indicating that TKA-1 activated the endogenous PDGF-R in a ligand-independent fashion.

EXAMPLE 7
TKA-1 promotes reorganization of actin cables

The effect of PDGF stimulation and TKA-1 expression on actin reorganization, as visualized by staining with TRITC-labeled phalloidin, was examined in NIH3T3 and NIH3T3/TKA-1 cells.

Serum-starved NIH3T3 cells and TKA-1 -expressing NIH3T3 cells were fixed with either no addition, stimulation with 5 ng/ml PDGF for 10 min, 30 min (E and F), or 60 min, and stained with TRITC-labeled phalloidin to show actin filaments. Serum-starved NIH3T3 cells exhibited diffuse actin circles and actin stress fibers which, upon PDGF stimulation for 10 minutes, disappeared and reorganized in edge ruffles. Prolonged incubation with PDGF resulted in partial reappearance of stress fibers, indicating that this was a transient effect. In contrast, NIH3T3 cells stably expressing TKA-1 displayed no actin stress fibers after serum starvation. Actin is diffusely organized in small circles within the cytoplasma and in minor edge ruffles, which upon PDGF stimulation became reorganized in pronounced ruffles and microspikes. Prolonged incubation with PDGF resulted in the disappearance of microspikes and the reappearance of small actin circles around the nucleus, but prevented the regeneration of stress fibers.

Although certain embodiments and examples have been used to describe the present invention, it will be apparent to those skilled in the art that changes to the embodiments and examples shown may be made without departing from the scope or spirit of the invention.

Those references not previously incorporated herein by reference, including both patent and nonpatent references, are expressly incorporated herein by reference for all purposes.

EXAMPLE 8
In Vitro Assay

The following protocol describes the procedures used to identify substances that interfere with the binding between a GLGF domain containing protein and a PDGF-R in an ELISA format.

REAGENTS AND SUPPLIES
1. Corning 96-well Elisa plates
Corning Catalog #25805-96
2. Anti β PDGF-R monoclonal antibody Genzyme (Cambridge, Mass. catalog number 1263-00
3. PBS (Dulbecco's Phosphate-Buffered Saline)
Gibco Catalog #450-1300EB
Formulation:
2.7 mM KCL
1.1 mM MgC12 (anhydrous)
138 mM NaCl
8.1 mN $Na_2HPO_4$ 4. TBST Buffer
Formulation:
  50 mM Tris pH7.2
  150 mM NaCl
  0.1% Triton X-100
5. Blocking Buffer
Formulation:
  5% Carnation Instant Milk in TBST
6. PDGF-R expressing cells such as 293 cells engineered to express PDGF-R and TKA-1.
7. HNTG* Buffer
Formulation:
  50 mM HEPES pH7.5
  150 mN NaCl
  10% Glycerol
  1% Triton×100
  1 mM Sodium vanadate
  2 mM EDTA
  5 mM Sodium pyrophosphate
  1 mM PMSF
8. TBST+1% DMSO
Formulation:
  1% DMSO in TBST Buffer
  (DMSO from Sigma, Catalog #2650)
9. NUNC 96-well V bottom polypropylene plates Applies Scientific Catalog # AS-72092
10. Purified TKA-1 antibody
11. Goat anti-rabbin IgG peroxidase conjugate BioSource International (Camarillo, Calif.) Catalog # NR5430, Lot #2103. Stored in Enzymology Lab, SUGEN, Inc., −20 C., 1 ml laiquots. Thaw aliquot once and leave a 4 C. for 4 weeks.
12. ABTS Solution
Formulation:
  100 mM Citric Acid (anhydrous), 250 mM Na2HPO4 pH 4.0, 0.5 mg/ml ABTS (2,2'-azzino-bis(3-ethylbenzthiazoline-6-sulfonic acid), (Sigma Catalog # A-1888) Keep solution in dark at 4 C. until ready to use.
13. Hydrogen peroxide 30% solution, Fisher Catalog #H325, store in the dark at 4 C. until ready to use.
14. ABTS/H2O2
Formulation:
  15 mls ABTS solution, add 2 ul H2O2 Prepare 5 minutes before use and leave at room temperature.
15. Purified TKA-1 protein

EXAMPLE 9

Procedure

1. Coat Corning 96-well ELISA plates with 0.5 ug anti-PDGFR monoclonal antibody. Bring final volume to 100 ul per well with PBS. Coat plates overnight at 4 C.

2. Remove unbound antibody from wells by inverting plate to remove the liquid. Wash 4x with TBST by filling wells and inverting plate between each wash. Pat the plate on a paper towel to remove excess liquid and bubbles.

3. Block plates with .5% milk in TBST. 150 ul per well. Incubate plate 30 minutes while shaking on a microtiter plate shaker.

4. Wash plate as described in step 2.

5. Grow cells to 80–90% confluency. Wash the cells 2× with PBS and lyse the cells in HNTG* buffer. Remove insoluble material by centrifugation (10,000×g, 10 min at 4 degree C.) and aliquot the lysate. Store the lysate at minus 80 degrees C. Add approximatley 50 ul cell lysate per well.

6. Wash 4× as described in step 2.

7. Dilute test substances 200 to 0.1 uM in 1% DMSO in 100 ul TBST and add concurrently with purified TKA-1 protein. Pre-incubated test substance and TKA-1 protein to wells containing the ELISA plate immobilized PDGF-R. Shake for 30 minutes.

8. After pre-incubation add 150 ul of the preincubated test substance and TKA-1 protein to wells containing the ELISA plate immobilized PDFG-R. Shake for 30 minutes.

9. Wash as described in step 2.

10. Dilute the anti-TKA-1 antiserum in TBST. Add 150 ul per well. Shake for 30 minutes.

11. Wash as described in step 2.

12. Dilute Goat anti-rabbit IgG-conjuugated horseradish peroxidase approxdimately 1:2500 in TBST. Add 150 ul per well. Incubate 30 minutes while shaking.

13. Wash as described in step 2 and rinse twoice with distilled water. Aspirate the liquid.

14. Add 100 ul of ABTS/H2O2 solution to well. Incubate 10 minutes while shaking.

15. Remove bubbles with slow stream of air.

16. Read plate on Dynatech MR5000 ELISA reader.
Test Filter: 410 nM
Reference Filter: 630 nM A similar assay can be used to identify substances that interfere with the binding between PDGFR and TKA-1. Assay plates are prepared as described in the previous protocol. Cells that express both proteins, such as the genetically engineered 293 cells described herein, are grown to 80–90% confluency then collected by trypsinization (0.25% trypsin-EDTA (Gibco)). The reaction is stopped with the addition of medium containing 10% fetal calf serum. The cells are suspended in fresh medium, and centrifuged once at 1500 rpm, rt, for 5 minutes. The cells are resuspended in fresh medium and tranferred to 96 well tissue culture plates (10,000–5,000 cells per well) in about 100 µl per will. The plates are then incubated at 37 degrees in 5% CO2 overnight.

Media in the wells is replaced by serum free growth media, 90 µl per well. Serial dilutions of test substance stocks (10 mg/ml) are diluted 1:10 into growth media and 10 µl added per well for a final concentration range of 100 µM to 1 nM. Control wells receive DMSO and medium only. The cells are incubated from 30 minutes to 2 hours at 37 degrees C., 5% CO2.

After incubation, the cell are washed twice with PBS and lysed as previously described. The cells are scraped from the micortiter wells and homogenized using a pipette tip and repeated aspirating and dispensing. The lysate is transferred to the previously prepared assay plate wells and allowed to bind for 1 hour at room temperature, shaking. The lysate is removed and the plate washed 4 time with TBST.

The ability of the test substance to interfere with binding can be measured directly using and anti TKA-1 antibody as previously described. Alternatively, as TKA-1 binding has ben shown to cause autophosphorylation of the PDGF-receptor, one can measure the amount of phosphotyrosine present on the bound PDFG-receptors. This can be done by the addition of anti-PY (rabbit polyclonal antiphosphotyrosine antibody prepared according the Fendly, et al., 1990, Cancer Research 50: 1550–1558) at 100 µl per well, diluted with TBST, then incubated, shaking, at room temperature for 30 minutes. THe anti-PY solution is removed, and the plate washed 4 time with TBST. The amount of antibody bound is detected in the same manner as previously described.

Other embodiments are within the following claims.

What is claimed is:

1. An isolated, enriched or purified nucleic acid comprising the nucleic acid sequence depicted in SEQ ID NO:1.

2. An isolated, enriched or purified nucleic acid comprising (a) a nucleotide sequence that encodes a polypeptide having the amino acid sequence SEQ ID NO:2, or (b) the complement of the nucleotide sequence of (a).

3. An isolated, enriched or purified nucleic acid comprising a nucleotide sequence that encodes a full length naturally occurring TKA-1 polypeptide, said nucleotide sequence able to hybridize to a nucleic acid of claim 2, wherein the washing conditions following hybridization are at least as stringent as 0.1×SSC, 0.1% SDS at 42° C.

4. An isolated, enriched or purified nucleic acid encoding a polypeptide comprising at least 200 contiguous amino acids of the polypeptide depicted in SEQ ID NO:2.

5. The nucleic acid of claim 4, wherein said nucleic acid encodes a polypeptide comprising at least 300 contiguous amino acids of the polypeptide depicted in SEQ ID NO:2.

6. The nucleic acid of claim 4, wherein said nucleic acid is human nucleic acid.

7. The nucleic acid of claim 4, wherein said nucleic acid differs from the nucleic acid sequence depicted in SEQ ID NO:1 by having no more than 10% base replacements.

8. The nucleic acid of claim 4, wherein said nucleic acid differs from the nucleic acid sequence depicted in SEQ ID NO:1 by having no more than 5% base replacements.

9. The nucleic acid of claim 2, 3, or 4 which is a genomic DNA.

10. The nucleic acid of claim 2, 3, or 4 which is a cDNA.

11. A recombinant molecule comprising a nucleic acid of claim 1, 2, 3, or 4.

12. An expression vector comprising a nucleic acid of claim 1, 2, 3, or 4 operably linked to a regulatory nucleotide sequence that controls expression of the nucleic acid in a host cell.

13. A host cell containing a nucleic acid of claim 1, 2, 3, or 4.

14. A host cell containing a nucleic acid of claim 1, 2, 3, or 4, said nucleic acid operably linked to a regulatory nucleotide sequence that controls expression of the nucleic acid in said host cell.

15. The host cell of claim 14 in which the host cell is prokaryotic.

16. The host cell of claim 14 in which the host cell is eukaryotic.

* * * * *